(12) United States Patent
Santos et al.

(10) Patent No.: US 7,071,157 B2
(45) Date of Patent: *Jul. 4, 2006

(54) DRYER-ADDED FABRIC SOFTENING ARTICLES AND METHODS

(75) Inventors: Bienvenido Alvarez Santos, Cincinnati, OH (US); Rhonda Jean Jackson, Cincinnati, OH (US); George Kavin Morgan, III, Hamilton, OH (US); Gregory Charles Maier, Cincinnati, OH (US); David James Dahlinger, Mason, OH (US); Ronald Edward Pegoli, Loveland, OH (US); Jiten Odhavji Dihora, Hamilton, OH (US); Zaiyou Liu, West Chester, OH (US); Kristin Marie Finley, Cincinnati, OH (US); Toan Trinh, Maineville, OH (US); Errol Hoffman Wahl, Cincinnati, OH (US); Stanley James Welling, Hamilton, OH (US); Barbara Kay Williams, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/903,674

(22) Filed: Jul. 30, 2004

(65) Prior Publication Data

US 2005/0003996 A1    Jan. 6, 2005

Related U.S. Application Data

(63) Continuation of application No. 10/137,467, filed on May 2, 2002, now Pat. No. 6,787,510.

(60) Provisional application No. 60/352,802, filed on Jan. 30, 2002, provisional application No. 60/288,767, filed on May 4, 2001.

(51) Int. Cl.
*C11D 17/00* (2006.01)

(52) U.S. Cl. .................. 510/520; 510/101; 510/516
(58) Field of Classification Search ............... 510/151, 510/520
See application file for complete search history.

(56) References Cited

U.S. PATENT DOCUMENTS

| 4,539,135 A | 9/1985 | Ramachandran et al. |
| 4,713,193 A | 12/1987 | Tai |
| 4,873,000 A | 10/1989 | Weller |
| 5,026,551 A | 6/1991 | Yorozu et al. |
| 5,336,665 A | 8/1994 | Garner-Gray et al. |
| 5,478,501 A | 12/1995 | Rau |
| 5,480,575 A | 1/1996 | Altieri et al. |
| 5,681,806 A | 10/1997 | Trinh et al. |
| 5,691,202 A | 11/1997 | Wan et al. |
| 5,858,959 A | 1/1999 | Surutzidis et al. |
| 5,955,419 A | 9/1999 | Barket, Jr. et al. |
| 5,965,515 A | 10/1999 | Rau |
| 5,993,854 A | 11/1999 | Needleman et al. |
| 5,997,901 A | 12/1999 | Mills |
| 6,787,510 B1 * | 9/2004 | Santos et al. ............... 510/101 |
| 2003/0013632 A1 | 1/2003 | Santos et al. |

FOREIGN PATENT DOCUMENTS

| CA | 2317022 | 11/2000 |
| EP | 0 816 484 A2 | 1/1998 |
| EP | 1 061 124 A1 | 12/2000 |
| WO | WO 93/08255 | 4/1993 |
| WO | WO 97/34981 | 9/1997 |
| WO | WO 98/27190 | 6/1998 |
| WO | WO 98/27192 | 6/1998 |
| WO | WO 99/21953 | 5/1999 |
| WO | WO 00/11134 | 3/2000 |

* cited by examiner

*Primary Examiner*—John R. Hardee
(74) *Attorney, Agent, or Firm*—David V. Upite

(57) ABSTRACT

A fabric conditioning article for use in a clothes dryer. The fabric conditioning article having a flexible sheet and a fabric conditioning composition deposited on the sheet. The fabric conditioning composition includes a fabric conditioning agent, perfumed particles and minor components. The perfume particles are a perfume composition incorporated into a porous mineral carrier such as clay and/or zeolite. Optionally, the perfume composition comprises low levels of unstable perfume components. Alternatively, the perfumed particles have a coating material encapsulating at least a portion of the particles. Optionally, the articles are packaged in a container having a moisture barrier to prevent premature release of the perfume therefrom.

26 Claims, No Drawings

DRYER-ADDED FABRIC SOFTENING ARTICLES AND METHODS

CROSS REFERENCE TO RELATED APPLICATIONS

This application is a continuation of U.S. patent application Ser. No. 10/137,467 filed May 2, 2002 now U.S. Pat. No. 6,787,510, which claims priority to U.S. Provisional Application Ser. Nos. 60/352,802, filed Jan. 30, 2002 and 60/288,767, filed May 4, 2001, the disclosure of which is incorporated by reference herein.

FIELD OF INVENTION

The present invention relates to an improvement in dryer-activated, e.g., dryer-added, laundry additive products and compositions. These products and/or compositions may be either in particulate form, compounded with other materials in. e.g., tablets, pellets, agglomerates, foams, etc., or preferably attached to a substrate.

BACKGROUND OF THE INVENTION

Due to economic considerations and convenience, consumer use of automated drying of laundered garments has increased in popularity in recent years. Not surprisingly, consumer use of dryer-activated additive compositions has also been increasing steadily. The popularity of these compositions has risen in part due to consumer desire to impart various properties to fabrics easily and quickly during the laundry process. A wide variety of ingredients have been suggested for use in laundry additive compositions to enhance the appearance and feel of fabrics. Fabric softeners provide both softening and anti-static benefits to fabrics. Perfumes deliver pleasing odors and freshness. Thus, dryer-activated additive products offer convenience, ease of use, and affordable economics to consumers as well as being superior delivery systems for desirable laundry additives such as perfumes and softeners.

U.S. Pat. No. 6,020,302 issued Feb. 1, 2000 to Leurentop, et al. discloses fabric softening compositions comprising a dye fixing agent and an amino-functional polymer for providing color care benefits to fabrics upon laundry treatments. Dryer-activated fabric softening compositions are disclosed and perfume, preferably protected by a carrier material such as zeolite, is noted as an optional component of these compositions.

European Patent Application No. EP 1 061 124 A1, published Dec. 20, 2000 (Givaudan S A) is directed to a method of preparing a protected fragrance matrix by absorbing the perfume on a solid absorbent. Use of the protected fragrance matrix on fabric softener sheets is also disclosed.

SUMMARY OF THE INVENTION

The present invention relates to fabric conditioning articles comprising perfumed particles for use in automatic clothes dryers. Methods for using the articles are also provided. Improved softness, perfume delivery from sheet substrates (lower m.p. range), and/or antistatic effects may also be provided.

The present invention relates to a dryer-added fabric conditioning article comprising a substrate in the form of a sheet and a fabric conditioning composition disposed on said sheet. The fabric conditioning composition comprises i) at least about 1% by weight of one or more fabric conditioning actives and ii) perfumed particles. The perfumed particles comprise porous inorganic carrier particles and a perfume composition absorbed and/or adsorbed on said carrier particles, wherein said perfume composition comprises less than about 30%, preferably less than about 15%, more preferably less than about 8%, even more preferably less than about 6%, still more preferably less than about 3%, and still more preferably less than about 1% by weight of the perfume composition of unstable perfume ingredients preferably selected from the group consisting of allylic alcohol ester, secondary alcohol ester, tertiary alcohol ester, allylic ketone, condensation product of amines and aldehydes, and mixtures thereof, more preferably selected from the group consisting of allylic alcohol ester, secondary alcohol ester, tertiary alcohol ester, allylic ketone, acetal, ketal, condensation product of amines and aldehydes, and mixtures thereof.

The present invention further provides a dryer-added fabric conditioning article comprising a substrate in the form of a sheet, and a fabric conditioning composition disposed on said sheet. The fabric conditioning composition comprising i) at least about 10% by weight of one or more fabric conditioning actives and ii) perfumed particles. The perfumed particles comprise porous inorganic carrier particles and a perfume composition absorbed and/or adsorbed on said carrier particles, wherein said perfumed particles further comprise a coating encapsulating at least a portion of said perfumed particles.

The articles of the present invention preferably comprise a package for enclosing the article(s). The package has a moisture barrier with a water vapor transmission rate of less than about 1.0 g $H_2O$/day/$m^2$, preferably less than about 0.5 g $H_2O$/day/$m^2$, more preferably less than about 0.3 g $H_2O$/day/$m^2$, and even more preferably about 0.1 g $H_2O$/day/$m^2$.

A process aspect of the present invention provides methods for depositing a fabric conditioning composition comprising a perfume composition on fabric so as to provide softness, antistatic effect and/or improved dry fabric odor. The methods comprise the step of contacting fabric with an article of the present invention.

All documents cited are, in relevant part, incorporated herein by reference; the citation of any document is not to be construed as an admission that it is prior art with respect to the present invention.

DETAILED DESCRIPTION OF THE INVENTION

The present invention relates to dryer-activated fabric conditioning articles comprising a substrate and a fabric conditioning composition comprising (i) one or more fabric conditioning actives, and (ii) perfumed particles comprising a porous inorganic carrier. The compositions and articles deliver superior perfume deposition including improved dry fabric odor that more closely represents the formulated perfume composition as well as a more intense dry fabric odor after storage.

I. Substrate

In the preferred embodiments, the present invention encompasses articles of manufacture or products. Representative articles are those that are adapted to be employed in an automatic laundry dryer, of the types disclosed in U.S. Pat. No. 3,989,631 Marsan, issued Nov. 2, 1976; U.S. Pat. No. 4,055,248, Marsan, issued Oct. 25, 1977; U.S. Pat. No. 4,073,996, Bedenk et al., issued Feb. 14, 1978; U.S. Pat. No.

4,022,938, Zaki et al., issued May 10, 1977; U.S. Pat. No. 4,764,289, Trinh, issued Aug. 16, 1988; U.S. Pat. No. 4,808,086, Evans et al., issued Feb. 28, 1989; U.S. Pat. No. 4,103,047, Zaki et al., issued Jul. 25, 1978; U.S. Pat. No. 3,736,668, Dillarstone, issued Jun. 5, 1973; U.S. Pat. No. 3,701,202, Compa et al., issued Oct. 31, 1972; U.S. Pat. No. 3,634,947, Furgal, issued Jan. 18, 1972; U.S. Pat. No. 3,633,538, Hoeflin, issued Jan. 11, 1972; and U.S. Pat. No. 3,435,537, Rumsey, issued Apr. 1, 1969; and U.S. Pat. No. 4,000,340, Murphy et al., issued Dec. 28, 1976, all of said patents being incorporated herein by reference. Other substrates, methods for preparing such substrates, and methods of incorporating fabric conditioning compositions onto such substrates are disclosed in International Patent Publication Nos. WO 00/27991, published May 18, 2000 and WO 00/65141, published Nov. 2, 2000.

In a preferred substrate article embodiment, the fabric conditioning compositions are provided as an article of manufacture in combination with a dispensing means such as a flexible substrate that effectively releases the composition in an automatic laundry (clothes) dryer. Such dispensing means can be designed for single usage or for multiple uses. The dispensing means can also be a "carrier material" that releases the fabric conditioning composition and then is dispersed and/or exhausted from the dryer.

The dispensing means will normally carry an effective amount of fabric conditioning composition. Such effective amount typically provides sufficient softness, antistatic effect and/or perfume deposition for at least one treatment of a minimum load in an automatic laundry dryer. Amounts of the fabric conditioning composition irrespective of load size for a single article can vary from about 0.1 g to about 100 g, preferably from about 0.1 g to about 20 g, most preferably from about 0.1 g to about 10 g.

Highly preferred paper, woven or nonwoven "absorbent" substrates useful herein are fully disclosed in U.S. Pat. No. 3,686,025, Morton, issued Aug. 22, 1972, which is incorporated herein by reference. It is known that most substances are able to absorb a liquid substance to some degree, however, the term "absorbent" as used herein, is intended to mean a substance with an absorbent capacity (i.e., a parameter representing a substrate's ability to take up and retain a liquid) from about 4 to about 12, preferably from about 5 to about 7, times its weight of water.

Another substrate comprises a sponge material releasably enclosing enough fabric conditioning composition to effectively impart softness, antistatic and/or perfume deposition during several cycles of clothes. This multi-use article can be made by incorporating about 20 grams of the fabric conditioning composition into the sponge material. Other dispensing means include synthetic foams, towels-like substrates, particles (tablets, pellets, granules, etc) and dispensers affixed to the dryer wall.

II. Fabric Conditioning Compositions

The articles of the present invention also comprise a fabric conditioning composition for imparting one or more fabric care benefits such as softening, anti-static, color protection, etc., to fabrics. The fabric conditioning compositions comprise one or more fabric conditioning actives, perfumed particles and optionally other minor components.

A. Fabric Conditioning Actives

The compositions of the present invention contain from at least about 1% to about 90%, preferably from about 10% to about 50%, more preferably from about 15% to about 40% of one or more fabric conditioning actives. Preferably, the fabric conditioning active(s) is a fabric softening active and/or an antistatic active.

The fabric softening actives can be one or a mixture of a quaternary ammonium compound, a tertiary amine and or its salts, an ethoxylated fatty material, a fatty acid or a mixture thereof. Examples of fabric softening actives that are especially useful in the articles are the compositions described in U.S. Pat. No. 4,103,047, Zaki et al., issued Jul. 25, 1978; U.S. Pat. No. 4,237,155, Kardouche, issued Dec. 2, 1980; U.S. Pat. No. 3,686,025, Morton, issued Aug. 22, 1972; U.S. Pat. No. 3,849,435, Diery et al., issued Nov. 19, 1974: and U.S. Pat. No. 4,073,996, Bedenk, issued Feb. 14, 1978; said patents are hereby incorporated herein by reference. Other fabric softening actives are disclosed hereinafter.

Quaternary Ammonium Compounds

Particularly preferred cationic fabric softeners for substrate articles include quaternary ammonium salts such as dialkyl dimethylammonium chlorides, methylsulfates and ethylsulfates wherein the alkyl groups can be the same or different and contain from about 14 to about 22 carbon atoms. Examples of such preferred materials include ditallowalkyldimethylammonium methylsulfate (DTDMAMS), distearyldimethylammonium methylsulfate, dipalmityldimethylammonium methylsulfate and dibehenyldimethylammonium methylsulfate.

Yet another preferred fabric softening active is an ester quaternary ammonium compound (EQA) selected from Formulas II, III, IV, V, and mixtures thereof.

Formula II comprises:

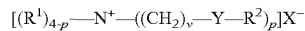

$$[(R^1)_{4-p}-N^+-((CH_2)_v-Y-R^2)_p]X^-$$

wherein each Y=—O—(O)C—, or —C(O)—O—; p=1 to 3; each v=is an integer from 1 to 4, and mixtures thereof; each $R^1$ substituent is a short chain $C_1$–$C_6$, preferably $C_1$–$C_3$, alkyl group, e.g., methyl (most preferred), ethyl, propyl, and the like, benzyl and mixtures thereof; each $R^2$ is a long chain, saturated and/or unsaturated (Iodine Value of from about 3 to about 60), $C_8$–$C_{30}$ hydrocarbyl, or substituted hydrocarbyl substituent and mixtures thereof; and the counterion, $X^-$, can be any softener-compatible anion, for example, methylsulfate, ethylsulfate, chloride, bromide, formate, sulfate, lactate, nitrate, benzoate, and the like, preferably methylsulfate.

It will be understood that substituents $R^1$ and $R^2$ of Formula II can optionally be substituted with various groups such as alkoxyl or hydroxyl groups. The preferred compounds can be considered to be diester quaternary ammonium salts (DEQA). At least about 25% of the DEQA is in the diester form, and from 0% to about 40%, preferably less than about 30%, more preferably less than about 20%, can be EQA monoester (e.g., only one —Y—$R^2$ group).

As used herein, when the diester is specified, it will include the monoester that is normally present. For the optimal antistatic benefit the percentage of monoester should be as low as possible, preferably less than about 2.5%. The level of monoester present can be controlled in the manufacturing of the EQA.

EQA compounds prepared with fully saturated acyl groups are excellent softeners. However, it has now been discovered that compounds prepared with at least partially unsaturated acyl groups have advantages (i.e., antistatic benefits) and are highly acceptable for consumer products when certain conditions are met. Variables that must be adjusted to obtain the benefits of using unsaturated acyl groups include the Iodine Value of the fatty acids, the odor of fatty acid starting material, and/or the EQA. Any reference to Iodine Value values hereinafter refers to Iodine Value of fatty acyl groups and not to the resulting EQA compound.

Some highly desirable, readily available sources of fatty acids such as tallow, possess odors that remain with the compound EQA despite the chemical and mechanical processing steps which convert the raw tallow to finished EQA. Such sources must be deodorized, e.g., by absorption, distillation (including stripping such as steam stripping), etc., as is well known in the art. In addition, care must be taken to minimize contact of the resulting fatty acyl groups to oxygen and/or bacteria by adding antioxidants, antibacterial agents, etc.

Generally, hydrogenation of fatty acids to reduce polyunsaturation and to lower Iodine Value to insure good color and odor stability leads to a high degree of trans configuration in the molecule. Therefore, diester compounds derived from fatty acyl groups having low Iodine Value values can be made by mixing fully hydrogenated fatty acid with touch hydrogenated fatty acid at a ratio which provides an Iodine Value of from about 3 to about 60. The polyunsaturation content of the touch hardened fatty acid should be less than about 5%, preferably less than about 1%. During touch hardening the cis/trans isomer weight ratios are controlled by methods known in the art such as by optimal mixing, using specific catalysts, providing high $H_2$ availability, etc.

It has been found that a solvent may be used to facilitate processing of the Formula II EQA and/or of the fabric softening composition containing the EQA Formula II.

It has also been found that for good chemical stability of the diester quaternary compound in molten storage, water levels in the raw material must be minimized to preferably less than about 8% and more preferably less than about 5%. Storage temperatures should be kept as low as possible and still maintain a fluid material, ideally in the range of from about 45° C. to about 70° C. The optimum storage temperature for stability and fluidity depends on the specific Iodine Value of the fatty acid used to make the diester quaternary and the level/type of solvent selected. Also, exposure to oxygen should be minimized to keep the unsaturated groups from oxidizing. It can therefore be important to store the material under a reduced oxygen atmosphere such as a nitrogen blanket. It is important to provide good molten storage stability to provide a commercially feasible raw material that will not degrade noticeably in the normal transportation/storage/handling of the material in manufacturing operations.

The following are non-limiting examples of EQA Formula II (wherein all long-chain alkyl substituents are straight-chain):

Saturated $(C_2H_5)_2{}^+N(CH_2CH_2OC(O)C_{17}H_{35})_2$ $(CH_3SO_4)^-$ $(HO\text{—}CH(CH_3)CH_2)(CH_3)^+N(CH_2CH_2OC(O)C_{15}H_{31})_2$ $Br^-$ $(CH_3)(C_2H_5)^+N(CH_2CH_2OC(O)C_{13}H_{27})_2$ $(HCOO)^-$ $(C_3H_7)(C_2H_5)^+N(CH_2CH_2OC(O)C_{11}H_{23})_2$ $(CH_3SO_4)^-$

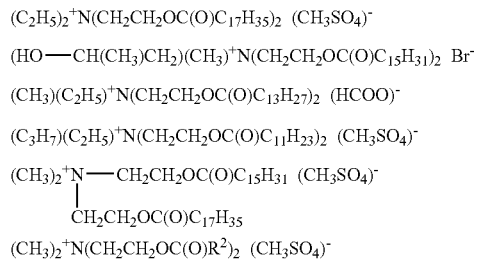

$(CH_3)_2{}^+N(CH_2CH_2OC(O)R^2)_2$ $(CH_3SO_4)^-$

-continued
$(CH_2CH_2OH)(CH_3)^+N(CH_2CH_2OC(O)R^2)_2$ $(CH_3SO_4)^-$ where —C(O)R² is derived from saturated tallow.

Unsaturated $(C_2H_5)_2{}^+N(CH_2CH_2OC(O)C_{17}H_{33})_2$ $(CH_3SO_4)^-$ $(HO\text{—}CH(CH_3)CH_2)(CH_3)^+N(CH_2CH_2OC(O)C_{15}H_{29})_2$ $Br^-$ $(C_2H_5)^+N(CH_2CH_2OC(O)C_{17}H_{33})_2$ $Cl^-$ $(CH_3)(C_2H_5)^+N(CH_2CH_2OC(O)C_{13}H_{27})_2$ $(C_6H_5COO)^-$

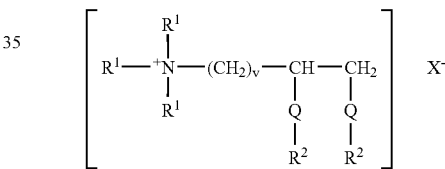

$(CH_2CH_2OH)(CH_3)^+N(CH_2CH_2OC(O)R^2)_2$ $(CH_2SO_4)^-$ $(CH_3)_2{}^+N(CH_2CH_2OC(O)R^2)_2$ $(CH_3SO_4)^-$ $(HOCH_2CH_2)(CH_3)^+N(CH_2CH_2OC(O)R^2)_2$ $(CH_3SO_4)^-$ where —C(O)R² is derived from partially hydrogenated tallow or modified tallow having the characteristics set forth herein.

In addition to Formula II compounds, the compositions and articles of the present invention comprise EQA compounds of Formula III:

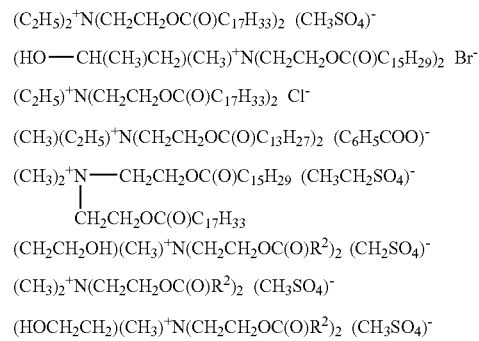

wherein, for any molecule: each Q is —O—C(O)— or —C(O)—O—; each R¹ is $C_1$–$C_4$ alkyl or hydroxy alkyl; R² and v are defined hereinbefore for Formula II; and wherein preferably R¹ is a methyl group, v is 1, Q is —O—C(O)—, each R² is $C_{14}$–$C_{18}$, and X⁻ is methyl sulfate.

The straight or branched alkyl or alkenyl chains, R², have from about 8 to about 30 carbon atoms, preferably from about 14 to about 18 carbon atoms, more preferably straight chains having from about 14 to about 18 carbon atoms.

Tallow is a convenient and inexpensive source of long chain alkyl and alkenyl materials.

A specific example of a Formula III EQA compound suitable for use in the fabric softening compositions herein is: 1,2-bis(tallowyl oxy)-3-trimethyl ammoniopropane methylsulfate (DTTMAPMS).

Other examples of suitable Formula III EQA compounds of this invention are obtained by, e.g., replacing "tallowyl" in the above compounds with, for example, cocoyl, lauryl, oleyl, stearyl, palmityl, or the like; replacing "methyl" in the above compounds with ethyl, propyl, isopropyl, butyl, isobutyl, t-butyl, or the hydroxy substituted analogs of these radicals; and/or replacing "methylsulfate" in the above compounds with chloride, ethylsulfate, bromide, formate, sulfate, lactate, nitrate, and the like, but methylsulfate is preferred.

In addition to Formula II and Formula III compounds, the compositions and articles of the present invention comprise EQA compounds of Formula IV:

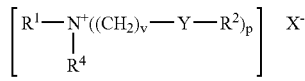

wherein $R^4$=a short chain $C_1$–$C_4$ alcohol; p is 2; $R^1$, $R^2$, v, Y, and $X^-$ are as previously defined for Formula II.

A specific example of a Formula IV compound suitable for use in the fabric softening compositions herein is N-methyl-N,N-di-(2-($C_{14}$–$C_{18}$-acyloxy) ethyl), N-2-hydroxyethyl ammonium methylsulfate. A preferred compound is N-methyl, N,N-di-(2-oleyloxyethyl) N-2-hydroxyethyl ammonium methylsulfate.

Compositions of the present invention may also comprise Formula V compounds:

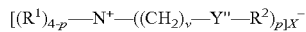

wherein $R^1$, $R^2$, p, v, and $X^-$ are previously defined in Formula II; and

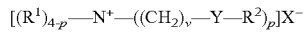

and mixtures thereof, wherein at least one Y''' group is

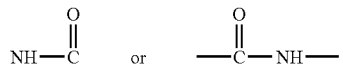

An example of this compound is methyl bis (oleyl amidoethyl) 2-hydroxyethyl ammonium methyl sulfate.

Preferably, the fabric softening active of the present invention is a quaternary ammonium compound.

The compounds herein can be prepared by standard esterification and quaternization reactions, using readily available starting materials. General methods for preparation are disclosed in U.S. Pat. No. 4,137,180, which is incorporated herein by reference.

Tertiary Amines and Salts Thereof

Another fabric conditioning active useful in the articles of the present invention is a carboxylic acid salt of a tertiary amine and/or ester amine having the formula:

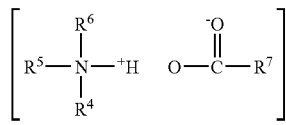

wherein $R^5$ is a long chain aliphatic group containing from about 8 to about 30 carbon atoms; $R^6$ and $R^4$ are the same or different from each other and are selected from the group consisting of aliphatic groups containing containing from about 1 to about 30 carbon atoms, hydroxyalkyl groups of the Formula $R^8$ OH wherein $R^8$ is an alkylene group of from about 2 to about 30 carbon atoms, and alkyl ether groups of the formula $R^9O(C_nH_{2n}O)_m$ wherein $R^9$ is alkyl and alkenyl of from about 1 to about 30 carbon atoms and hydrogen, n is 2 or 3, and m is from about 1 to about 30; wherein $R^4$, $R^5$, $R^6$, $R^8$, and $R^9$ chains can be ester interrupted groups; and wherein $R^7$ is selected from the group consisting of unsubstituted alkyl, alkenyl, aryl, alkaryl and aralkyl of about 8 to about 30 carbon atoms, and substituted alkyl, alkenyl, aryl, alkaryl, and aralkyl of from about 1 to about 30 carbon atoms wherein the substituents are selected from the group consisting of halogen, carboxyl, and hydroxyl, said composition having a thermal softening point of from about 35° C. to about 100° C.

This component can provide superior odor and/or improved fabric softening performance, compared to similar articles which utilize primary amine or ammonium compounds as the sole fabric conditioning agent. Either $R^4$, $R^5$, $R^6$, $R^7$, $R^8$, and/or $R^9$ chains can contain unsaturation.

Preferably, $R^5$ is an aliphatic chain containing from about 12 to about 30 carbon atoms, $R^6$ is an aliphatic chain of from about 1 to about 30 carbon atoms, and $R^4$ is an aliphatic chain of from about 1 to about 30 carbon atoms. Particularly preferred tertiary amines for static control performance are those containing unsaturation; e.g., oleyldimethylamine and/or soft tallowdimethylamine.

Examples of preferred tertiary amines as starting material for the reaction between the amine and carboxylic acid to form the tertiary amine salts are: lauryldimethylamine, myristyldimethylamine, stearyldimethylamine, tallowdimethylamine, coconutdimethylamine, dilaurylmethyl amine, distearylmethyl amine, ditallowmethylamine, oleyldimethylamine, dioleylmethylamine, lauryldi(3-hydroxypropyl)amine, stearyldi(2-hydroxyethyl)amine, trilaurylamine, laurylethylmethylamine, and

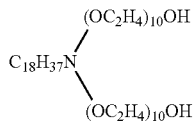

Preferred fatty acids are those wherein $R^7$ is a long chain, unsubstituted alkyl or alkenyl group of from about 8 to about 30 carbon atoms, more preferably from about 11 to about 17 carbon atoms.

Examples of specific carboxylic acids as a starting material are: formic acid, acetic acid, lauric acid, myristic acid, palmitic acid, stearic acid, oleic acid, oxalic acid, adipic acid, 12-hydroxy stearic acid, benzoic acid, 4-hydroxy benzoic acid, 3-chloro benzoic acid, 4-nitro benzoic acid, 4-ethyl benzoic acid, 4-(2-chloroethyl)benzoic acid, phenylacetic acid, (4-chlorophenyl)acetic acid, (4-hydroxyphenyl) acetic acid, and phthalic acid.

Preferred carboxylic acids are stearic, oleic, lauric, myristic, palmitic, and mixtures thereof.

The amine salt can be formed by a simple addition reaction, well known in the art and disclosed in U.S. Pat. No. 4,237,155, Kardouche, issued Dec. 2, 1980, which is incorporated herein by reference. Excessive levels of free amines may result in odor problems, and generally free amines provide poorer softening performance than the amine salts.

Preferred amine salts for use herein are those wherein the amine moiety is a $C_8$–$C_{30}$ alkyl or alkenyl dimethyl amine or a di-$C_8$–$C_{30}$ alkyl or alkenyl methyl amine, and the acid moiety is a $C_8$–$C_{30}$ alkyl or alkenyl monocarboxylic acid. The amine and the acid, respectively, used to form the amine salt will often be of mixed chain lengths rather than single chain lengths, since these materials are normally derived from natural fats and oils, or synthetic processed which produce a mixture of chain lengths. Also, it is often desirable to utilize mixtures of different chain lengths in order to modify the physical or performance characteristics of the softening composition.

Specific preferred amine salts for use in the present invention are oleyldimethylamine stearate, stearyldimethylamine stearate, stearyldimethylamine myristate, stearyldimethylamine oleate, stearyldimethylamine palmitate, distearylmethylamine palmitate, distearylmethylamine laurate, and mixtures thereof. A particularly preferred mixture is oleyldimethylamine stearate and distearylmethylamine myristate, in a ratio of 1:10 to 10:1, preferably about 1:1.

Nonionic Softening Actives

A softening active that can also be employed in the present invention is a nonionic fabric softener material. Typically, such nonionic fabric softener materials have an HLB of from about 2 to about 9, and more typically from about 3 to about 7. In general, the materials selected should be relatively crystalline and higher melting, (e.g., >25° C.).

The level of optional nonionic softener in the solid composition is typically from about 0.1% to about 50%, preferably from about 5% to about 30%.

Preferred nonionic softeners are fatty acid partial esters of polyhydric alcohols, or anhydrides thereof, wherein the alcohol or anhydride contains from about 2 to about 18 and preferably from about 2 to about 8 carbon atoms, and each fatty acid moiety contains from about 8 to about 30 and preferably from about 12 to about 20 carbon atoms. Typically, such softeners contain from about one to about 3 and preferably about 2 fatty acid groups per molecule.

The polyhydric alcohol portion of the ester can be ethylene glycol, glycerol, poly (e.g., di-, tri-, tetra, penta-, and/or hexa-) glycerol, xylitol, sucrose, erythritol, pentaerythritol, sorbitol or sorbitan.

The fatty acid portion of the ester is normally derived from fatty acids having from about 8 to about 30 and preferably from about 12 to about 22 carbon atoms. Typical examples of said fatty acids being lauric acid, myristic acid, palmitic acid, stearic acid, oleic acid, and behenic acid.

Highly preferred optional nonionic softening agents for use in the present invention are $C_{10}$–$C_{26}$ acyl sorbitan esters and polyglycerol monostearate. Sorbitan esters are esterified dehydration products of sorbitol. The preferred sorbitan ester comprises a member selected from the group consisting of $C_{10}$–$C_{26}$ acyl sorbitan monoesters and $C_{10}$–$C_{26}$ acyl sorbitan diesters and ethoxylates of said esters wherein one or more of the unesterified hydroxyl groups in said esters contain from about 1 to about 6 oxyethylene units, and mixtures thereof. For the purpose of the present invention, sorbitan esters containing unsaturation (e.g., sorbitan monooleate) can be utilized.

Sorbitol, which is typically prepared by the catalytic hydrogenation of glucose, can be dehydrated in well known fashion to form mixtures of 1,4- and 1,5-sorbitol anhydrides and small amounts of isosorbides. (See U.S. Pat. No. 2,322,821, Brown, issued Jun. 29, 1943, incorporated herein by reference.)

The foregoing types of complex mixtures of anhydrides of sorbitol are collectively referred to herein as "sorbitan." It will be recognized that this "sorbitan" mixture will also contain some free, uncyclized sorbitol.

The preferred sorbitan softening agents of the type employed herein can be prepared by esterifying the "sorbitan" mixture with a fatty acyl group in standard fashion, e.g., by reaction with a fatty acid halide, fatty acid ester, and/or fatty acid. The esterification reaction can occur at any of the available hydroxyl groups, and various mono-, di-, etc., esters can be prepared. In fact, mixtures of mono-, di-, tri-, etc., esters almost always result from such reactions, and the stoichiometric ratios of the reactants can be simply adjusted to favor the desired reaction product.

For commercial production of the sorbitan ester materials, etherification and esterification are generally accomplished in the same processing step by reacting sorbitol directly with fatty acids. Such a method of sorbitan ester preparation is described more fully in MacDonald, "Emulsifiers: Processing and Quality Control", *Journal of the American Oil Chemists' Society*, Vol. 45, October 1968. Details, including formula, of the preferred sorbitan esters can be found in U.S. Pat. No. 4,128,484, incorporated hereinbefore by reference.

Certain derivatives of the preferred sorbitan esters herein, especially the "lower" ethoxylates thereof (i.e., mono-, di-, and tri-esters wherein one or more of the unesterified —OH groups contain one to about twenty oxyethylene moieties (Tweens®) are also useful in the composition of the present invention. Therefore, the term "sorbitan ester" is intended to include such derivatives.

For the purposes of the present invention, it is preferred that a significant amount of di- and tri-sorbitan esters are present in the ester mixture. Ester mixtures having from about 20–50% mono-ester, about 25–50% di-ester and about 10–35% of tri- and tetra-esters are preferred. Material which is sold commercially as sorbitan mono-ester (e.g., monostearate) typically contains significant amounts of di- and tri-esters. A typical analysis of commercial sorbitan monostearate indicates that it comprises about 27% mono-, about 32% di- and about 30% tri- and tetra-esters and is therefore a preferred material. Mixtures of sorbitan stearate and sorbitan palmitate having stearate/palmitate weight ratios varying between 10:1 and 1:10, and 1,5-sorbitan esters are also useful. In addition, both the 1,4- and 1,5-sorbitan esters are useful herein.

Other useful alkyl sorbitan esters for use in the softening compositions herein include sorbitan monolaurate, sorbitan monomyristate, sorbitan monopalmitate, sorbitan monobehenate, sorbitan monooleate, sorbitan dilaurate, sorbitan dimyristate, sorbitan dipalmitate, sorbitan distearate, sorbitan dibehenate, sorbitan dioleate, and mixtures thereof, and mixed tallowalkyl sorbitan mono- and di-esters. Such mixtures are readily prepared by reacting the foregoing hydroxy-substituted sorbitans, particularly the 1,4- and 1,5-sorbitans, with the corresponding acid, ester, or acid chloride in a simple esterification reaction. It is to be recognized, of course, that commercial materials prepared in this manner will comprise mixtures usually containing minor proportions of uncyclized sorbitol, fatty acids, polymers, isosorbide structures, and the like. In the present invention, it is preferred that such impurities are present at as low a level as practical.

The preferred sorbitan esters employed herein can contain up to about 15% by weight of esters of the $C_{20}$–$C_{26}$, and higher, fatty acids, as well as minor amounts of $C_8$, and lower, fatty esters.

Glycerol and polyglycerol esters, especially glycerol, diglycerol, triglycerol, and polyglycerol mono- and/or di-esters, preferably mono-, are also preferred herein (e.g., polyglycerol monostearate with a trade name of Radiasurf 7248). Glycerol esters can be prepared from naturally occurring triglycerides by normal extraction, purification and/or interesterification processes or by esterification processes of the type set forth hereinbefore for sorbitan esters. Partial esters of glycerin can also be ethoxylated to form usable derivatives that are included within the term "glycerol esters."

Useful glycerol and polyglycerol esters include monoesters with stearic, oleic, palmitic, lauric, isostearic, myristic, and/or behenic acids and the diesters of stearic, oleic, palmitic, lauric, isostearic, behenic, and/or myristic acids. It is understood that the typical mono-ester contains some di- and tri-ester, etc.

The "glycerol esters" also include the polyglycerol, e.g., diglycerol through octaglycerol esters. The polyglycerol polyols are formed by condensing glycerin or epichlorohydrin together to link the glycerol moieties via ether linkages. The mono- and/or diesters of the polyglycerol polyols are preferred, the fatty acyl groups typically being those described hereinbefore for the sorbitan and glycerol esters.

Fatty Acids

The fabric conditioning active in the articles of the present invention may further comprise one or more fatty acids. Typically, the fatty acid is present to improve the processability of the composition, and is admixed with any material, or materials, that are difficult to process, especially as a result of having a high viscosity. The fatty acid provides improved viscosity and/or processability, without harming softening or antistatic performance of the fabric conditioning composition.

Preferred fatty acids are those containing a long chain, unsubstituted alkenyl group of from about 8 to about 30 carbon atoms, more preferably from about 11 to about 18 carbon atoms. Examples of specific carboxylic acids are: oleic acid, linoleic acid, and mixtures thereof. Although unsaturated fatty acids are preferred, the unsaturated fatty acids can be used in combination with saturated fatty acids like stearic, palmitic, and/or lauric acids. Preferred carboxylic acids are oleic, linoleic, tallow fatty acids, and mixtures thereof.

Preferably, the fatty acid is added to the quaternization reaction mixture used to form the biodegradable quaternary ammonium compounds of Formulas II, III, and/or IV as described hereinbefore to lower the viscosity of the reaction mixture to less than about 1500 cps, preferably less than about 1000 cps, more preferably less than about 800 cps. The solvent level of added fatty acid is from about 5% to about 30%, preferably from about 10% to about 25%, more preferably from about 10% to about 20%. The unsaturated fatty acid can be added before the start of the quaternization reaction or, preferably, during the quaternization reaction when it is needed to reduce the viscosity which increases with increased level of quaternization. Preferably the addition occurs when at least about 60% of the product is quaternized. This allows for a low viscosity for processing while minimizing side reactions that can occur when the quaternizing agent reacts with the fatty acid. The quaternization reactions are well known and include, e.g., with respect to Formula I compounds, those processes described in U.S. Pat. No. 3,915,867, Kang et al., issued Oct. 28, 1975; U.S. Pat. No. 4,830,771, Ruback et al., issued May 16, 1989; and U.S. Pat. No. 5,296,622, Uphues et al., issued Mar. 22, 1994, all of said patents being incorporated herein by reference. The resulting quaternized biodegradable fabric softening actives can be used without removal of the unsaturated fatty acid, and, in fact, are more useful since the mixture is more fluid and more easily handled.

Another preferred type of fabric softener is described in detail in U.S. Pat. No. 4,661,269, Toan Trinh, Errol H. Wahl, Donald M. Swartley and Ronald L. Hemingway, issued Apr. 28, 1987, said patent being incorporated herein by reference B. Perfumed Particles 1. Porous Inorganic Carrier Particles A preferred porous carrier of the present invention is a porous zeolite having a multitude of pore openings. The term "zeolite" used herein refers to a crystalline aluminosilicate material. The structural formula of a zeolite is based on the crystal unit cell, the smallest unit of structure represented by $$M_{m/n}[(AlO_2)_m(SiO_2)_y] \cdot xH_2O$$

where n is the valence of the cation M, x is the number of water molecules per unit cell, m and y are the total number of tetrahedra per unit cell, and y/m is about 1 to about 100. Most preferably, y/m is about 1 to about 5. The cation M can be Group IA and Group IIA elements, such as sodium, potassium, magnesium, and calcium.

A suitable class of zeolites for use in the present invention is Zeolite A and zeolite 4A.

The zeolite that is preferred for use herein is a faujasite-type zeolite, including Type X Zeolite or Type Y Zeolite, both with a nominal pore size of about 8 Angstrom units, typically in the range of from about 7.4 to about 10 Angstrom units.

The aluminosilicate zeolite materials useful in the practice of this invention are commercially available. Methods for producing X and Y-type zeolites are well-known and available in standard texts. Preferred synthetic crystalline aluminosilicate materials useful herein are available under the designation Type X or Type Y.

For purpose of illustration, nonlimiting examples of the preferred Type X zeolites include:

$$Na_{86}[AlO_2]_{86}(SiO_2)_{106}] \cdot xH_2O, \tag{I}$$

$$K_{86}[AlO_2]_{86}(SiO_2)_{106}] \cdot xH_2O, \tag{II}$$

$$Ca_{40}Na_6[AlO_2]_{86}(SiO_2)_{106}] \cdot xH_2O, \tag{III}$$

$$Sr_{21}Ba_{22}[AlO_2]_{86}(SiO_2)_{106}] \cdot xH_2O, \tag{IV}$$

and mixtures thereof, wherein x is from about 0 to about 276. Zeolites of formula (I) and (II) have a nominal pore size or opening of 8.4 Angstroms units. Zeolites of formula (III) and (IV) have a nominal pore size or opening of 8.0 Angstroms units.

Similarly, nonlimiting examples of the preferred Type Y zeolites include:

$$Na_{56}[AlO_2]_{56} \cdot (SiO_2)_{136}] \cdot xH_2O, \tag{V}$$

$$K_{56}[AlO_2]_{56} \cdot (SiO_2)_{136}] \cdot xH_2O \tag{VI}$$

and mixture thereof, wherein x is from about 0 to about 276. Zeolites of formula (V) and (VI) have a nominal pore size or opening of 8.0 Angstroms units.

The zeolites used in the present invention are in particle form having an average particle size from about 0.5 microns to about 120 microns, preferably from about 0.5 microns to about 30 microns, as measured by standard particle size analysis technique.

More information about these and other zeolites, the preferred embodiments, including nonlimiting examples of different zeolite types are given in U.S. Pat. No. 5,691,303 issued Nov. 25, 1997 to Pan, et al., U.S. Pat. No. 6,221,826 issued Apr. 24, 2001 to Surutzidis, et al., and U.S. Pat. No. 6,245,732 issued Jun. 12, 2001 to Gallon, et al.

Hydrated zeolites are suitable for the compositions of the present invention, however preferred zeolites are dehydrated/activated zeolites. The Type X or Type Y Zeolites to be used herein preferably contain less than about 10% desorbable water, more preferably less than about 8% desorbable water, and even more preferably less than about 5% desorbable water. Activated zeolites can be obtained by heating the zeolites to a high temperature under normal atmospheric pressure, e.g., to 450° C. as disclosed in East German Patent Publication No. 248,508, published Aug. 12, 1987, and to about 150–350° C. for at least about 12 hours as disclosed in U.S. Pat. Nos. 5,691,303 issued Nov. 25, 1997, or heating the zeolites to a high temperature under reduced pressure, e.g., from about 0.001 to about 20 Torr, as disclosed in U.S. Pat. No. 5,691,303 issued Nov. 25, 1997.

Clay also can be a useful porous carrier for use in the present invention. The clay minerals which are useful herein include a wide variety of materials, included among which are smectite-type clays such as bentonite, montmorillonite; kaolinite, metakaolin; attapulgite, and mixtures thereof. These and other preferred clays are disclosed with more details in U.S. Pat. No. 4,539,135 issued Sep. 3, 1985.

2. Perfume Compositions

A wide variety of organic compounds are known for perfume uses, including organic materials having at least one reactive functional group such as ester, aldehyde, ketone, acetal, ketal, carbon-carbon double bond, and the like. Perfume ingredients according to the present invention can include more than one reactive functional group. More commonly, naturally occurring plant and animal oils and exudates comprising complex mixtures of various chemical components are known for use as perfumes. Non-limiting examples of common perfume ingredients that are useful in consumer products are given in U.S. Pat. No. 5,714,137 issued Feb. 3, 1998 to Trinh, et al. and U.S. Pat. No. 6,048,830 issued Apr. 11, 2000 to Gallon, et al.

Non-limiting examples of preferred perfume ingredients suitable for use in perfume compositions of the present invention are adoxal (2,6,10-trimethyl-9-undecen-1-al), amyl acetate, amyl salicylate, anisic aldehyde (4-methoxy benzaldehyde), bacdanol (2-ethyl-4-(2,2,3-trimethyl-3-cyclopenten-1-yl)-2-buten-1-ol), benzaldehyde, benzophenone, benzyl acetate, benzyl salicylate, 3-hexen-1-ol, cetalox (dodecahydro-3A,6,6,9A-tetramethylnaphtho[2,1B]-furan), cis-3-hexenyl acetate, cis-3-hexenyl salicylate, citronellol, coumarin, cyclohexyl salicylate, cymal (2-methyl-3-(para iso propyl phenyl)propionaldehyde), decyl aldehyde, ethyl vanillin, ethyl-2-methyl butyrate, ethylene brassylate, eucalyptol, eugenol, exaltolide (cyclopentadecanolide), florhydral (3-(3-isopropylphenyl) butanal), galaxolide (1,3,4,6,7,8-hexahydro-4,6,6,7,8,8-hexamethylcyclopenta-gamma-2-benzopyrane), gamma decal actone, gamma dodecalactone, geraniol, geranyl nitrile, helional (alpha-methyl-3,4, (methylenedioxy) hydrocinnamaldehyde), heliotropin, hexyl acetate, hexyl cinnamic aldehyde, hexyl salicylate, hydroxyambran (2-cyclododecyl-propanol), hydroxycitronellal, iso E super (7-acetyl-1,2,3,4,5,6,7,8-octahydro-1,1,6,7,tetramethyl naphthalene), iso eugenol, iso jasmone, koavone (acetyl di-isoamylene), lauric aldehyde, lrg 201 (2,4-dihydroxy-3,6-dimethyl benzoic acid methyl ester), lyral (4-(4-hydroxy-4-methyl-pentyl) 3-cylcohexene-1-carboxaldehyde), majantol (2,2-dimethyl-3-(3-methylphenyl)-propanol), mayol (4-(1-methylethyl) cyclohexane methanol), methyl anthranilate, methyl beta naphthyl ketone, methyl cedrylone (methyl cedrenyl ketone), methyl chavicol (1-methyloxy-4,2-propen-1-yl benzene), methyl dihydro jasmonate, methyl nonyl acetaldehyde, musk indanone (4-acetyl-6-tert butyl-1,1-dimethyl indane), nerol, nonalactone (4-hydroxynonanoic acid, lactone), norlimbanol (1-(2,2,6-trimethyl-cyclohexyl)-3-hexanol), P. T. bucinal (2-methyl-3(para tert butylphenyl) propionaldehyde), para hydroxy phenyl butanone, patchouli, phenyl acetaldehyde, phenyl ethyl acetate, phenyl ethyl alcohol, phenyl ethyl phenyl acetate, phenyl hexanol/phenoxanol (3-methyl-5-phenylpentanol), polysantol (3,3-dimethyl-5-(2,2,3-trimethyl-3-cyclopenten-1-yl)-4-penten-2-ol), rosaphen (2-methyl-5-phenyl pentanol), sandal wood, alpha-terpinene, tonalid/musk plus (7-acetyl-1,1,3,4,4,6-hexamethyl tetralin), undecalactone, undecavertol (4-methyl-3-decen-5-ol), undecyl aldehyde, undecylenic aldehyde, vanillin, and mixtures thereof.

Perfumes for incorporation into the porous mineral carriers and for use in the consumable compositions of the present invention can be relatively simple in their compositions or more preferably can comprise highly complex mixtures of natural and synthetic chemical ingredients, chosen to provide a desired odor benefit. Perfume compositions herein preferably comprises at least about 6 perfume ingredients, preferably at least about 7 perfume ingredients, more preferably at least about 8 perfume ingredients, even more preferably at least about 9 perfume ingredients, and still more preferably at least about 10 perfume ingredients. Most common perfume ingredients which are derived from natural or synthetic sources can be composed of a multitude of minor components. When each such material is used in the formulation of the preferred perfume compositions of the present invention, it is counted as a single ingredient, for the purpose of defining the invention. Furthermore, in the perfume art, some materials having no odor or very faint odor are used as diluents, or extenders, or fixatives, and/or combinations thereof. Non-limiting examples of these materials are dipropylene glycol, diethyl phthalate, triethyl citrate, isopropyl myristate, and benzyl benzoate. These materials are used for, e.g., diluting and stabilizing some other perfume ingredients. These materials are not counted in the formulation of the preferred perfume compositions of the present invention.

Perfume compositions useful in the compositions and articles of the present invention preferably comprise less than about 100% aldehyde and/or acetal perfume ingredients. In addition, such perfume compositions preferably comprise less than 45% terpinol, by weight of the perfume composition.

Perfume ingredients are more or less volatile, and are perceptible in the vapor phase. The more volatile ingredients can rapidly escape from the consumable composition, or when the perfume is treated on a substrate. In other products, such as laundry products, most of the perfume is lost to the laundry process resulting in only a small amount of perfume being deposited onto the washed fabrics. Laundry products can comprise perfume compositions comprising substantive perfume ingredients that are better retained on fabrics after the washing process. Such substantive perfume ingredients are characterized by having a boiling point equal to or higher than about 250° C. and a ClogP value equal to or greater than about 3, as being disclosed in U.S. Pat. No. 5,500,138 issued to Bacon, et al. Perfume absorbed onto and/or into a porous carrier to form perfumed particles is another approach to reduce the perfume release and/or perfume loss. However, as noted in the Background of the Invention above, such perfume particles are not sufficiently stable in storage for many commercial applications, due to a premature release of the perfume from the carrier.

Stable and Unstable Perfume Ingredients

It is now discovered that surprisingly, many common perfume ingredients are not compatible with porous mineral carrier materials, such as clays and zeolites, particularly dehydrated/activated zeolites. It is found that some perfume ingredients are decomposed, degraded and/or catalyzed upon incorporation into a porous mineral carrier material, to form materials that are undesirable and/or not intended in the original perfume compositions. Furthermore, some of these ingredients can cause discoloration in some consumable compositions.

An unstable perfume ingredient can be identified by loading a liquid perfume composition comprising at least 6 perfume ingredients including the perfume ingredient being studied into a sample of activated/dehydrated zeolite 13X, according to the procedure given hereinbelow, and stored under anhydrous condition for about 24 hours. The perfume ingredients are then extracted with acetone to be recovered as free perfume and analyzed by gas chromatography to determine its stability. A perfume ingredient is characterized as an "unstable perfume ingredient" if at least about 50% of that ingredient, preferably at least 65%, more preferably at least about 80%, and even more preferably at least about 95% of that ingredient is decomposed into other by-products, and not recovered from the extraction.

Non-limiting examples of the unstable perfume ingredients that are not suitable for use in the present invention preferably include ingredients selected from the group consisting of allylic alcohol ester, secondary alcohol ester, tertiary alcohol ester, allylic ketone, condensation product of amines and aldehydes, and mixtures thereof, and more preferably include ingredients selected from the group consisting of allylic alcohol ester, secondary alcohol ester, tertiary alcohol ester, allylic ketone, acetal, ketal, condensation product of amines and aldehydes, and mixtures thereof.

"Allylic alcohol" refers to an alcohol molecule wherein the carbon atom carrying the alcoholic hydroxyl group is covalently bonded to a carbon-carbon double bond in the alpha and beta positions, namely, having the general structure C(OH)—C=C. Non-limiting examples of allylic alcohol ester perfume ingredients include allyl amyl glycolate, allyl anthranilate, allyl benzoate, allyl butyrate, allyl caprate, allyl caproate, allyl cinnamate, allyl cyclohexane acetate, allyl cyclohexane butyrate, allyl cyclohexane propionate, allyl heptoate, allyl nonanoate, allyl salicylate, amyl cinnamyl acetate, amyl cinnamyl formate, cinnamyl formate, cinnamyl acetate, cyclogalbanate, geranyl acetate, geranyl acetoacetate, geranyl benzoate, geranyl cinnamate, methallyl butyrate, methallyl caproate, neryl acetate, neryl butyrate, amyl cinnamyl formate, alpha-methyl cinnamyl acetate, methyl geranyl tiglate, mertenyl acetate, farnesyl acetate, fenchyl acetate, geranyl anthranilate, geranyl butyrate, geranyl iso-butyrate, geranyl caproate, geranyl caprylate, geranyl ethyl carbonate, geranyl formate, geranyl furoate, geranyl heptoate, geranyl methoxy acetate, geranyl pelargonate, geranyl phenylacetate, geranyl phthalate, geranyl propionate, geranyl iso-propoxyacetate, geranyl valerate, geranyl iso-valerate, trans-2-hexenyl acetate, trans-2-hexenyl butyrate, trans-2-hexenyl caproate, trans-2-hexenyl phenylacetate, trans-2-hexenyl propionate, trans-2-hexenyl tiglate, trans-2-hexenyl valerate, beta-pentenyl acetate, alpha-phenyl allyl acetate, prenyl acetate, trichloromethylphenylcarbinyl acetate, and mixtures thereof.

"Secondary alcohol" refers to an alcohol molecule-wherein the carbon atom carrying the alcoholic hydroxyl group is covalently bonded to a hydrogen atom and two carbon atoms, namely, having the general structure C—CH(OH)—C. Non-limiting examples of secondary alcohol ester perfume ingredients include secondary-n-amyl acetate, ortho-tertiary-amyl cyclohexyl acetate, isoamyl benzyl acetate, secondary-n-amyl butyrate, amyl vinyl carbinyl acetate, amyl vinyl carbinyl propionate, cyclohexyl salicylate, dihydro-nor-cyclopentadienyl acetate, dihydro-nor-cyclopentadienyl propionate, isobornyl acetate, isobornyl salicylate, isobornyl valerate, flor acetate, frutene, 2-methylbuten-2-ol-4-acetate, methyl phenyl carbinyl acetate, 2-methyl-3-phenyl propan-2-yl acetate, prenyl acetate, 4-tert-butyl cyclohexyl acetate, verdox (2-tert-butyl cyclohexyl acetate), vertenex, (4-tert-butylcyclohexyl acetate), Violiff (carbonic acid 4-cycloocten-1-yl methyl ester), ethenyl-iso-amyl carbinylacetate, fenchyl acetate, fenchyl benzoate, fenchyl-n-butyrate, fenchyl isobutyrate, laevo-menthyl acetate, dl-menthyl acetate, menthyl anthranilate, menthyl benzoate, menthyl-iso-butyrate, menthyl formate, laevo-menthyl phenylacetate, menthyl propionate, menthyl salicylate, menthyl-iso-valerate, cyclohexyl acetate, cyclohexyl anthranilate, cyclohexyl benzoate, cyclohexyl butyrate, cyclohexyl-iso-butyrate, cyclohexyl caproate, cyclohexyl cinnamate, cyclohexyl formate, cyclohexyl heptoate, cyclohexyl oxalate, cyclohexyl pelargonate, cyclohexyl phenylacetate, cyclohexyl propionate, cyclohexyl thioglycolate, cyclohexyl valerate, cyclohexyl-iso-valerate, methyl amylacetate, methyl benzyl carbinyl acetate, methyl butyl cyclohexanyl acetate, 5-methyl-3-butyl-tetrahydropyran-4-yl acetate, methyl citrate, methyl-iso-campholate, 2-methyl cyclohexyl acetate, 4-methyl cyclohexyl acetate, 4-methyl cyclohexyl methyl carbinyl acetate, methyl ethyl benzyl carbinyl acetate, 2-methylheptanol-6-acetate, methyl heptenyl acetate, alpha-methyl-n-hexyl carbinyl formate, methyl-2-methylbutyrate, methyl nonyl carbinyl acetate, methyl phenyl carbinyl acetate, methyl phenyl carbinyl anthranilate, methyl phenyl carbinyl benzoate, methyl phenyl carbinyl-n-butyrate, methyl phenyl carbinyl-iso-butyrate, methyl phenyl carbinyl caproate, methyl phenyl carbinyl caprylate, methyl phenyl carbinyl cinnamate, methyl phenyl carbinyl formate, methyl phenyl carbinyl phenylacetate, methyl phenyl carbinyl propionate, methyl phenyl carbinyl salicylate, methyl phenyl carbinyl-iso-valerate, 3-nonanyl acetate, 3-nonenyl acetate, nonane diol-2:3-acetate, nonynol acetate, 2-octanyl acetate, 3-octanyl acetate, n-octyl acetate, secondary-octyl-iso-butyrate, beta-pentenyl acetate, alpha-phenyl allyl acetate, phenylethyl methyl carbinyl-iso-valerate, phenylethyleneglycol diphenylacetate, phenylethyl ethnyl carbinyl acetate, phenylglycol diacetate, seconday-phenylglycol monoacetate, phenylglycol monobenzoate, isopropyl caprate, isopropyl caproate, isporppyl caprylate, isopropyl cinnamate, para-isopropyl cyclohexanyl acetate, propylglycol diacetate, propyleneglycol di-isobutyrate, propyleneglycol dipropionate, isopropyl-n-heptoate, isopropyl-n-hept-1-yne carbonate, isopropyl pelargonate, isopropyl propionate, isopropyl undecylenate, isopropyl-n-valerate, isopropyl-n-valerate, isopropyl-iso-valerate, isopropyl sebacinate, isopulegyl acetate, isopulegyl acetoacetate, isopulegyl isobutyrate, isopulegyl formate, thymyl propionate, alpha-2,4-trimethyl cyclohexane methylacetate, trimethyl cyclohexyl acetate, vanillin triacetate, vanillylidene diacetate, vanillyl vanillate, and mixtures thereof.

"Teriary alcohol" refers to an alcohol molecule wherein the carbon atom carrying the alcoholic hydroxyl group is covalently bonded to three other carbon atoms, namely, having the general structure

Non-limiting examples of tertiary alcohol ester include tertiary-amyl acetate, caryophyllene acetate, cedrenyl acetate, cedryl acetate, dihydromyrcenyl acetate, dihydroterpinyl acetate, dimethyl benzyl carbinyl acetate, dimethyl benzyl carbinyl isobutyrate, dimethyl heptenyl acetate, dimethyl heptenyl formate, dimethyl heptenyl propionate, dimethyl heptenyl-iso-butyrate, dimethyl phenylethyl carbinyl acetate, dimethyl phenylethyl carbinyl-iso-butyrate, dimethyl phenylethyl carbinyl-iso-valerate, dihydro-nor-dicyclopentadienyl acetate, dimethyl benzul carbinyl butyrate, dimethyl benzyl carbinyl formate, dimethyl benzyl carbinyl propionate, dimethyl phenylethyl carbinyl-n-butyrate, dimethyl phenyletyl carbinyl formate, dimethyl phenylethyl carbinyl propionate, elemyl acetate, ethinyl cyclohexylacetate, eudesmyl acetate, eugenyl cinnamate, eugenyl formate, iso-eugenyl formate, eugenyl phenylacetate, isoeudehyl phenylacetate, guaiyl acetate, hydroxycitronellyl ethylcarbonate, linallyl acetate, linallyl anthranilate, linallyl benzoate, linallyl butyrate, linallyl iosbutyrate, linallyl carproate, linallyl caprylate, linallyl cinnamate, linallyl citronellate, linallyl formate, linallyl heptoate, linallyl-N-methylanthranilate, linallyl methyltiglate, linallyl pelargonate, linallyl phenylacetate, linallyl propionate, linallyl pyruvate, linallyl salicylate, linallyl-n-valerate, linallyl-iso-valerate, methylcyclopentenolone butyrate, methyl cyclopentenolone propionate, methyl ethyl phenyl carbinyl acetate, methyl heptin carbonate, methyl nicotinate, myrcenyl acetate, myrcenyl formate, myrcenyl propionate, cis-ocimenyl acetate, phenyl salicylate, terpinyl acetate, terpinyl anthranilate, terpinyl benzoate, terpinyl-n-butyrate, terpinyl-iso-butyrate, terpinyl cinnamate, terpinyl formate, terpinyl phenylacetate, terpinyl propionate, terpinyl-n-valerate, terpinyl-iso-valerate, tributyl acetylcitrate, and mixtures thereof.

Some alcohols of the unstable alcohol ester perfume ingredients can be both allylic and secondary, or both allylic and tertiary. Non-limiting examples of these ingredients are amyl vinyl carbinyl acetate, amyl vinyl carbinyl propionate, hexyl vinyl carbinyl acetate, 3-nonenyl acetate, 4-hydroxy-2-hexenyl acetate, linallyl anthranilate, linallyl benzoate, linallyl butyrate, linallyl iosbutyrate, linallyl carproate, linallyl caprylate, linallyl cinnamate, linallyl citronellate, linallyl formate, linallyl heptoate, linallyl-N-methylanthranilate, linallyl methyltiglate, linallyl pelargonate, linallyl phenylacetate, linallyl propionate, linally pyruvate, linallyl salicylate, linallyl-n-valerate, linallyl-iso-valerate, myrtenyl acetate, nerolidyl acetate, nerolidyl butyrate, beta-pentenyl acetate, alpha-phenyl allyl acetate, and mixtures thereof.

"Allylic ketone" refers to a ketone molecule wherein the ketone functional group is covalently bonded to a carbon-carbon double bond in the alpha and beta positions, namely, having a general structure C—C(=O)—C=C. Non-limiting examples of allylic ketone perfume ingredients include acetyl furan, allethrolone, allyl ionone, allyl pulegone, amyl cyclopentenone, benzylidene acetone, benzylidene acetophenone, alpha iso methyl ionone, 4-(2,6,6-trimetyl-1-cyclohexen-1-yl)-3-buten-2-one, beta damascone (1-(2,6,6-trimethylcyclohexen-1-yl)-2-buten-1-one), damascenone (1-(2,6,6-trimethyl-1,3-cyclohexadien-1-yl)-2-buten-1-one), delta damascone (1-(2,6,6-trimethyl-3-cyclo-hexen-1-yl)-2-buten-1-one), alpha ionone (4-(2,6,6-trimethyl-1-cyclohexenyl-1-yl)-3-buten-2-one), beta ionone (4-(2,6,6-trimethyl-1-cyclohexen-1-yl)-3-butene-2-one), gamma methyl ionone (4-(2,6,6-trimethyl-2-cyclohexyl-1-yl)-3-methyl-3-buten-2-one), pulegone, and mixtures thereof.

"Acetal" refers to an acetal molecule wherein the aldehyde functional group is covalently bonded to two oxygen atoms of two hydroxyl groups at the same carbonyl carbon, namely, having a general structure C—CH(OC)$_2$. Non-limiting examples of acetal perfume ingredients include acetaldehyde-benzyl-beta-methoxyethyl acetal, acetaldehyde-di-iso-amyl acetal, acetaldehyde-di-pentandeiol acetal, acetaldehyde-di-n-propyl acetal, 10 acetaldehyde-ethyl-trans-3-hexenyl acetal, acetaldehyde-phenylethyleneglycol acetal, acetaldehyde phenylethyl-n-propylacetal, cinnamic aldehyde dimethyl acetal, acetaldehyde-benzyl-beta-methoxyethyl acetal, acetaldehyde-di-iso-amylacetal, acetaldehyde diethylacetal, acetaldehyde-di-cis-3-hexenyl acetal, acetaldehyde-di pentanediol acetal acetaldehyde-di-n-propyl acetal, acetaldehyde-ethyl-trans-3-hexenyl acetal, acetaldehyde-phenylethyleneglycol acetal, acetaldehyde phenylethyl-n-propylacetal, acetylvanillin dimethylacetal, alpha-amylcinnamic aldehyde-di-iso-propyl acetal, p-tertiary-amyl phenoxy acetaldehyde diethylacetal, anisaldehyde-diethylacetal, anisaldehyde-dimethylacetal, iso-apiole, benzaldehyde diethylacetal, benzaldehyde-di-(ethyleneglycol monobutylether) acetal, benzaldehyde dimethylacetal, benzaldehyde ethyleneglycolacetal, benzaldehyde glyceryl acetal, benzaldehydepropyleneglycol acetal, cinnamic aldehyde diethyl acetal, citral diethyl acetal, citral dimethyl acetal, citral propyleneglycol acetal, alpha-methylcinnamic aldehyde diethylacetal, alpha-cinnamic aldehyde dimethylacetal, phenylacetaldehyde-2,3-butyleneglycol acetal, phenylacetaldehyde citronellyl methyl acetal, phenylacetaldehyde diallylacetal, phenylacetaldehyde diamylacetal, phenylacetaldehyde dibenzylacetal, phenylacetaldehyde dibutyl acetal, phenylacetaldehyde diethylacetal, phenylacetaldehyde digeranylacetal, phenylacetaldehyde dimethylacetal, phenylacetaldehyde ethyleneglycol acetal, phenylacetalde glycerylacetal, citronellal cyclomonoglycolacetal, citronellal diethylacetal, citronellal dimethylacetal, citronellal diphenylethyl acetal, geranoxyacetaldehyde diethylacetal, and mixtures thereof.

"Ketal" refers to a ketal molecule wherein the carbonyl functional group of a ketone is covalently bonded to two oxygen atoms of two hydroxyl groups at the same carbonyl carbon, namely, having a general structure CC(OC)$_2$C. Non-limiting examples of acetal perfume ingredients include acetone diethylkatal, acetone dimethylketal, acetophenone diethyl ketal, methyl amyl catechol ketal, methyl butyl catechol ketal, and mixtures thereof.

Non-limiting examples of perfume ingredients being condensation products of amines and alhehydes, and not being preferred in the perfume compositions of the present invention include anisaldehyde-methylanthranilate, aurantiol (hydroxycitronellal methylanthranilate), verdantiol (4-tert-butyl-alpha-methyldihydrocinnamaldehyde methyl anthranilate), vertosine (2,4-dimethyl-3-cyclohexene carbaldehyde), hydroxycitronellal ethylanthranilate, hydroxycitronellal linallylanthranilate, methyl-N-(4-(4-hydroxy-4-methylpentyl)-3-cyclohexenyl-methylidene)-anthranilate, methylnaphthylketone-methylanthranilate, methyl nonyl acetaldehyde methylanthranilate, methyl-N-(3,5,5-trimethyl hexylidene) anthranilate, vanillin methyl anthranilate, and mixtures thereof.

While not wishing to be bound by theory, it is believed that the porous mineral carriers of the present invention exert a catalytic effect that promotes the decomposition of these particular perfume ingredients.

The perfume compositions that are suitable for use in the present invention typically comprises less than about 30%, preferably less than about 15%, more preferably less than about 8%, even more preferably less than about 6%, yet even more preferably less than about 3%, and even more preferably less than about 1%, by weight of the perfume composition, of unstable perfume ingredients, preferably selected from the group consisting of allylic alcohol ester, secondary alcohol ester, tertiary alcohol ester, allylic ketone, condensation product of amines and aldehydes, and mixtures thereof, more preferably, allylic alcohol ester, secondary alcohol ester, tertiary alcohol ester, allylic ketone, acetal, ketal, condensation product of amines and aldehydes, and mixtures thereof.

A "stable" perfume ingredient can be loaded into activated/dehydrated zeolite 13× in the same manner without substantial degradation, with typically at least about 50%, preferably at least 65%, more preferably at least about 80%, and even more preferably at least about 95% of that ingredient not decomposed into other by-products. A perfume molecule is also considered as "stable" when it is isomerized in the zeolite loading process into another structure with the same molecular weight. Non-limiting examples of such stable perfume ingredients include alpha-pinene and beta-pinene.

Thus, the perfume compositions that are suitable for use in the present invention typically comprises at least about 70%, preferably at least about 85%, more preferably at least about 93%, even more preferably at least about 95%, yet even more preferably at least about 97%, and even more preferably at least about 99%, by weight of the perfume composition, of stable perfume ingredients.

Porous mineral carriers provide an advantageous benefit in that they can retain perfume ingredients for a slow release, including non-substantive ingredients. Therefore, preferably, perfume compositions that are incorporated into the porous mineral carrier, for use in the compositions and articles of the present invention comprise at least about 30%, preferably at least about 50%, more preferably at least about 65%, of non-substantive perfume ingredients which are characterized by having a boiling point equal to or lower than about 250° C.

Non-limiting examples of such non-substantive perfume ingredients include amyl acetate, amyl propionate, anethol, anisic aldehyde, anisole, benzaldehyde, benzyl acetate, benzyl acetone, benzyl alcohol, benzyl butyrate, benzyl formate, benzyl iso valerate, benzyl propionate, camphor gum, carvacrol, laevo-carveol, d-carvone, laevo-carvone, citral (neral), citronellol, citronellyl acetate, citronellyl isobutyrate, citronellyl nitrile, citronellyl propionate, para-cresol, para-cresyl methyl ether, cyclohexyl ethyl acetate, cuminic alcohol, cuminic aldehyde, cyclal C (3,5-dimethyl-3-cyclo-hexene-1-carboxaldehyde), para-cymene, decyl aldehyde, dimethyl benzyl carbinol, dimethyl octanol, diphenyl oxide, dodecalactone, ethyl acetate, ethyl aceto acetate, ethyl amyl ketone, ethyl benzoate, ethyl butyrate, ethyl hexyl ketone, ethyl phenyl acetate, eucalyptol, eugenol, fenchyl alcohol, geraniol, geranyl nitrile, hexenol, beta gamma hexenol, hexenyl acetate, cis-3-hexenyl acetate, hexenyl isobutyrate, cis-3-hexenyl tiglate, hexyl acetate, hexyl formate, hexyl neopentanoate, hexyl tiglate, hydratropic alcohol, hydroxycitronellal, indole, alpha-irone, isoamyl alcohol, isobutyl benzoate, isomenthone, isononyl acetate, isononyl alcohol, isobutyl quinoline, isomenthol, para-isopropyl phenylacetaldehyde, isopulegol, isopulegyl acetate, isoquinoline, cis-jasmone, lauric aldehyde (dodecanal), ligustral (2,4-dimethyl-3-cyclohexene-1-carboxaldehyde), linalool, linalool oxide, menthone, methyl acetophenone, para-methyl acetophenone, methyl amyl ketone, methyl anthranilate, methyl benzoate, methyl benzyl acetate, methyl chavicol, methyl eugenol, methyl heptenone, methyl heptine carbonate, methyl heptyl ketone, methyl hexyl ketone, methyl nonyl acetaldehyde, methyl octyl acetaldehyde, methyl salicylate, myrcene, neral, nerol, gamma-nonalactone, nonyl acetate, nonyl aldehyde, allo-ocimene, octalactone, octyl alcohol (octanol-2), octyl aldehyde, (d-limonene), phenoxy ethanol, phenyl acetaldehyde, phenyl ethyl acetate, phenyl ethyl alcohol, phenyl ethyl dimethyl carbinol, propyl butyrate, rose oxide, 4-terpinenol, alpha-terpineol, terpinolene, tonalid (6-acetyl-1,1,3,4,4,6-hexamethyl tetrahydronaphthalene), undecenal, veratrol (ortho-dimethoxybenzene).

Low Odor Detection Threshold

The perfume composition of the present invention can additionally comprise perfume ingredients with low odor detection threshold. The odor detection threshold of an odorous material is the lowest vapor concentration of that material that can be olfactorily detected. The odor detection threshold and some odor detection threshold values are discussed in, e.g., "Standardized Human Olfactory Thresholds", M. Devos, et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character, and are especially useful in the compositions of the present invention. These materials can be present at low levels in the perfume compositions of the present invention, typically less than about 20% by weight of the total perfume compositions of the present invention.

Nonlimiting examples of perfume ingredients that have a significantly low detection threshold, useful in the composition of the present invention, are, ambrox (1,5,5,9-tetramethyl-1,3-oxatricyclotridecane), anethole, bacdanol (2-ethyl-4-(2,2,3-trimethyl-3-cyclopenten-1-yl)-2-buten-1-ol), benzyl acetone, benzyl salicylate, butyl anthranilate, calone, cetalox (2-ethyl-4-(2,2,3-trimethyl-3-cyclopenten-1-yl)-2-buten-1-ol), cinnamic alcohol, coumarin, Cyclal C (3,5-dimethyl-3-cyclohexene-1-carboxaldehyde), cymal (2-methyl-3-(para iso propylphenyl)propionaldehyde), 4-decenal, dihydro isojasmonate, gamma-dodecalactone, ebanol, ethyl anthranilate, ethyl-2-methyl butyrate, ethyl vanillin, eugenol, florhydral (3-(3-isopropylphenyl)butanol), fructone (ethyl-2-methyl-1,3-dioxolane-2-acetate), heliotropin, herbavert (3,3,5-trimethylcyclohexyl-ethyl ether), cis-3-hexenyl salicylate, indole, iso cyclo citral, isoeugenol, alpha-isomethylionone, keone, lilial (para-tertiary butyl alpha-methyl hydrocinnamic aldehyde), linalool, lyral (4-(4-hydroxy-4-methyl-pentyl)3-cylcohexene-1-carboxaldehyde), methyl heptine carbonate, methyl anthranilate, methyl dihydrojasmonate, methyl isobutenyl tetrahydropyran, methyl beta naphthyl ketone, methyl nonyl ketone, beta naphthol methyl ether, nerol, para-anisic aldehyde, para hydroxy phenyl butanone, phenyl acetaldehyde, gamma-undecalactone, undecylenic aldehyde, vanillin, and mixtures thereof. Some of the low odor detection perfume ingredients are also non-substantive perfume ingredients.

In a preferred embodiment, the perfume composition of the present invention does not consist of 0.2% allyl amyl glycolate, 0.31% damascenone, 0.51% decyl aldehyde, 15.27% dihydro iso jasmonate, 1.02% helional, 14.97% ionone gamma methyl, 20.37% linalool, 1.02% myrcene, 15.27% p.t. bucinal, 0.51% para methyl acetophenone, 20.37% phenyl ethyl alcohol, and 10.18% undecavertol, by weight of the perfume composition. In another preferred embodiment, the perfume composition of the present invention does not consist of 10% benzyl salicylate, 5% coumarin, 0.2% ethyl vanillin, 10% ethylene brassylate, 15% galaxolide, 20% hexyl cinnamic aldehyde, 10% gamma methyl ionone, 15% lilial, 5% methyl dihydrojasmonate, 5% patchouli, and 3% tonalid.

A zeolite carrier having perfume incorporated into the zeolite is referred to as a perfumed particle. The total "zeolite payload" refers to the maximum amount of perfume which can be incorporated into the zeolite carrier. The zeolite payload is less than about 20%, typically less than about 18.5%, by weight of the loaded particle, given the limits on the pore volume of the zeolite. It is to be recognized, however, that the perfumed particles may comprise perfume in an amount that exceeds the payload level, because of excess perfume that is not incorporated into the zeolite pores. Therefore, the perfumed particles of the present invention particles may comprise more than 20% by weight of perfume.

The compositions and articles of the present invention can additionally comprise free perfume that is not incorporated in the porous mineral carriers. Free perfume can comprise stable and/or unstable perfume ingredients. As disclosed hereinabove, in the context of fabric care compositions such as laundry detergent and/or fabric conditioning compositions, a substantial amount of the free perfume that is added to the wash and/or the rinse cycle is lost with the water and in the subsequent drying cycle. It is therefore preferable that at least about 25%, more preferably at least about 50%, and even more preferably at least about 70%, by weight of free perfume when present, is composed of substantive ingredients that tend to remain on fabrics after the laundry washing and drying process. Substantive perfume ingredients are characterized by having a boiling point equal to or higher than about 250° C. and a ClogP value equal to or greater than about 3, as disclosed in U.S. Pat. No. 5,500,138 issued to Bacon, et al. Non-limiting examples of the preferred substantive perfume ingredients for use in the free perfume compositions of the present invention are listed as "enduring perfume ingredients" in PCT Publication WO 01/85888 published Nov. 15, 2001.

Pro-Fragrances

Optionally, the compositions and articles of the present invention can comprise one or more pro-fragrances, pro-perfumes, pro-accords, and mixtures thereof, known collectively as "pro-fragrances". Preferably the pro-fragrances are not incorporated into the dehydrated/activated porous mineral carriers. Non-limiting examples of pro-fragrances include acetal pro-fragrances, ketal pro-fragrances, ester pro-fragrances, hydrolysable inorganic-organic pro-fragrances, and mixtures thereof. The preferred pro-fragrances are described with more details in PCT Publication WO 01/85888 published Nov. 15, 2001.

Optionally, free, stable and/or unstable perfume ingredients, including non-substantive perfume ingredients can be incorporated or encapsulated in other types of perfume carriers, for use in the compositions and articles of the present invention. Thus, the perfume can be encapsulated in the form of molecular encapsulation, such as inclusion in a complex with cyclodextrin, coacevate microencapsulation wherein the perfume droplet is enclosed in a solid wall material, and "cellular matrix" encapsulation wherein solid particles contain perfume droplets stably held in cells or perfume is embedded in, e.g., starch or sugar matrix. These preferred optional perfume carriers, which can be useful in the present invention, are disclosed in PCT Publication WO 01/85888 published Nov. 15, 2001.

Following are non-limiting examples of suitable perfume compositions of the present invention:

Perfume A

| Perfume Ingredients | Wt. % |
|---|---|
| Amyl salicylate | 1 |
| Anisic aldehyde | 1 |
| Citral | 4 |
| Citronellol | 5 |
| Citronellyl nitrile | 3 |
| para Cymene | 2 |
| Decyl aldehyde | 1 |
| Dihydro myrcenol | 15 |
| Geranyl nitrile | 3 |
| beta gamma Hexenol | 0.3 |
| cis-3-Hexenyl acetate | 0.2 |
| Hexyl cinnamic aldehyde | 5 |
| Hexyl salicylate | 3 |
| alpha-Ionone | 2 |
| cis-Jasmone | 1 |
| Linalool | 8 |
| Linalyl acetate | 5 |
| gamma-Methyl ionone | 3 |
| Myrcene | 1.5 |
| Nerol | 3 |
| Orange terpenes | 15 |
| P.T. Bucinal | 5 |
| Patchouli | 1 |
| Phenyl hexanol | 5 |
| beta-Pinene | 3 |
| alpha-Terpineol | 4 |
| Total | 100 |

Perfume A comprises about 10% by weight of unstable perfume ingredients.

Perfume B

| Perfume Ingredients | Wt. % |
|---|---|
| Aurantiol | 3 |
| Benzophenone | 3 |
| Citronellol | 15 |
| Citronellyl nitrile | 3 |
| Decyl aldehyde | 1 |
| Dihydro myrcenol | 5 |
| Dimethyl octanol | 5 |
| Diphenyl oxide | 1 |
| Geraniol | 7 |
| Geranyl acetate | 3 |
| Geranyl formate | 3 |
| Hexyl cinnamic aldehyde | 10 |
| alpha-Ionone | 3 |
| Isobornyl acetate | 4 |
| gamma-Methyl ionone | 4 |
| P.T. Bucinal | 10 |
| Phenyl ethyl alcohol | 15 |
| Terpineol | 5 |
| Total | 100 |

Perfume B comprises about 20% by weight of unstable perfume ingredients.

Perfume C

| Perfume Ingredients | Wt. % |
| --- | --- |
| Bisabolene | 3 |
| Camphene | 1 |
| Caryophyllene | 1 |
| para-Cymene | 1 |
| Eucalyptol | 1.5 |
| Fenchyl alcohol | 1 |
| Geranyl acetate | 2 |
| d-Limonene | 49 |
| Linalool | 3 |
| Myrcene | 2 |
| alpha-Pinene | 1.5 |
| beta-Pinene | 2 |
| Terpinene-4-ol | 2 |
| Terpineol | 10 |
| Terpinolene | 20 |
| Total | 100 |

Perfume C comprises about 10% by weight of unstable perfume ingredients.

Perfume D

| Perfume Ingredients | Wt. % |
| --- | --- |
| Citral | 4 |
| Frutene | 15 |
| d-Limonene | 50 |
| Linalyl Acetate | 6 |
| Methyl Dihydrojasmonate | 18 |
| alpha-Pinene | 4 |
| beta-Pinene | 3 |
| Total | 100 |

Perfume D comprises about 21% by weight of unstable perfume ingredients.

Perfume E

| Perfume Ingredients | Wt. % |
| --- | --- |
| Camphor gum | 0.5 |
| para-Cymene | 0.5 |
| Dihydro myrcenol | 1 |
| Dihydro terpineol | 2.5 |
| Dimethyl benzyl carbinol | 1 |
| Dimetol | 1.5 |
| Eucalyptol | 1 |
| Fenchyl alcohol | 1.5 |
| Isononyl alcohol | 0.5 |
| Tetrahydro linalool | 45 |
| Tetrahydro myrcenol | 44 |
| Verdox | 1 |
| Total | 100 |

Perfume E comprises about 1% by weight of unstable perfume ingredients.

Perfume F

| Perfume Ingredients | Wt. % |
| --- | --- |
| Benzyl Propionate | 2 |
| Citral | 3 |
| Citronellyl nitrile | 2 |
| Decyl aldehyde | 0.5 |
| Dihydro myrcinol | 10 |
| Eucalyptol | 2 |
| Fenchyl alcohol | 0.5 |
| Flor acetate | 7 |
| Frutene | 5 |
| Geranyl nitrile | 3 |
| beta gamma Hexenol | 0.5 |
| Linalool | 7 |
| Linalyl acetate | 5 |
| Methyl dihydro jasmonate | 5 |
| Octyl aldehyde | 0.5 |
| Orange terpenes | 30 |
| para-Cymene | 1.5 |
| Phenyl hexanol | 5 |
| alpha-Pinene | 2.5 |
| alpha-Terpineol | 2 |
| Terpinyl acetate | 2 |
| Tetrahydro linalool | 3 |
| Verdox | 1 |
| Total | 100 |

Perfume F comprises about 20% by weight of unstable perfume ingredients.

Perfumes G and H

| Perfume Ingredients | G Wt. % | H Wt. % |
| --- | --- | --- |
| Amyl salicylate | 8 | — |
| Benzyl acetate | 8 | 8 |
| Benzyl Salicylate | — | 2 |
| Citronellol | 7 | 25 |
| Dihydromyrcenol | 2 | — |
| Eugenol | 4 | — |
| Flor acetate | 8 | — |
| Galaxolide | 1 | — |
| Geraniol | 5 | — |
| Hexyl cinnamic aldehyde | 2 | — |
| Hydroxycitronellal | 3 | — |
| Lilial | 2 | — |
| Linalool | 6 | 9 |
| Linalyl acetate | 5 | — |
| Lyral | 3 | — |
| Methyl dihydrojasmonate | 3 | — |
| Nerol | 2 | — |
| Orange terpenes | 7 | 10 |
| Phenoxy ethyl propionate | — | 3 |
| Phenylethyl acetate | 5 | 15 |
| Phenylethyl alcohol | 7 | 15 |
| alpha-Terpineol | 5 | 13 |
| alpha-Terpinene | 5 | — |
| Tetrahydromyrcenol | 2 | — |
| Total | 100 | 100 |

Perfume G comprises about 13% by weight of unstable perfume ingredients. Perfume H does not comprises an appreciable amount of unstable perfume ingredients.

Optional Cyclodextrin/Perfume Complexes and Free Perfume

The compositions and articles herein may also contain from about 0.5% to about 60%, preferably from about 1% to about 50%, more preferably 2% to about 25%, cyclodextrin/ perfume inclusion complexes and/or free perfume, as disclosed in U.S. Pat. No. 5,139,687, Borcher et al., issued Aug. 18, 1992; and U.S. Pat. No. 5,234,610, Gardlik et al., issued Aug. 10, 1993, the disclosures of which are herein incorporated by reference. Where a perfume is not to be incorporated into/onto a porous inorganic carrier, such as in the case of unstable perfume ingredients, such ingredients are preferably present in the composition as a free perfume or complexed with cyclodextrin.

Many known perfume compositions are designed to be relatively substantive to maximize their odor effect on substrates. However, a special advantage of perfume delivery via the perfumed particles and perfume/cyclodextrin complexes is that non-substantive perfumes are also effective. If a product contains both free and complexed perfume, the escaped perfume from the complex contributes to the overall perfume odor intensity, giving rise to a longer lasting perfume odor impression.

As disclosed in U.S. Pat. No. 5,234,610, Gardlik, et al., issued Aug. 3, 1993, said patent being incorporated herein by reference, by adjusting the levels of free perfume and perfume/CD complex it is possible to provide a wide range of unique perfume profiles in terms of timing (release) and/or perfume identity (character). Solid, dryer-activated compositions are a uniquely desirable way to apply the cyclodextrins, since they are applied at the very end of a fabric treatment regimen when the fabric is clean and when there are almost no additional treatments that can remove the cyclodextrin before the next wash cycle.

3. Preparation of Perfumed Particles

Prior to incorporation of perfume the zeolite is first activated/dehydrated so that the zeolite contains less than about 10% and preferably less than about 5% water. This activation/dehydration may be accomplished by heating the material between about 150° C. to about 350° C., for at least about 12 hours. Optionally, activation/dehydration of the zeolite may be facilitated by heating the material at reduced pressures (from about 0.001 to about 20 Torr). After activation, the perfume is slowly and thoroughly mixed with the activated zeolite and, optionally, heated to about 60° C. for about 2 hours to accelerate absorption equilibrium within the zeolite particles. The mixture of perfume and zeolite tends to generate heat as the perfume is incorporated therein and it is preferable to cool the mixture during this mixing. The perfume/zeolite mixture is then cooled to room temperature and is in the form of a free-flowing powder.

The mixing and entrapment of perfume active into the perfume carrier can be carried out using various techniques known in the art of adsorption, absorption, and agglomeration. The perfume active (100% active or diluted in a solvent) can be sprayed onto a bed of carrier particles, followed by mixing. Alternatively, the perfume can be loaded in the vapor or superheated phase. Another option is to use a rotating drum mixer, and spraying on the perfume active using a single fluid, two-fluid, ultrasonic, or other nozzle technology. One can also use continuous agglomerating equipment, well-known to those familiar in the art, to entrap perfume in the carrier particles. Most often, perfume actives are adsorbed or absorbed onto perfume carriers such as zeolite by simply mixing the perfume active with the carrier in a bulk mixer, typically a rotating drum mixer.

Examples A–C provide examples of various methods and techniques that may be used to prepare the perfumed particles.

EXAMPLE A

Activated zeolite 13X (about 850 g) was loaded into a 4 liter plow-type jacketed mixer. The mixer was activated and 150 g of perfume was added to the mixer via a pressure nozzle. Cooling water at 15° C. was circulated through the mixer jacket to remove the heat generated by the adsorption of the perfume. The mixer continued to operate for 10 minutes. After 10 minutes, the product was discharged from the mixer and collected.

EXAMPLE B

Activated zeolite 13X (about 21.25 g) was placed in an 8 oz. glass jar. 3.75 g of perfume was added dropwise to the jar of zeolite. The jar was sealed and shaken for 2 minutes.

EXAMPLE C

Activated zeolite 13X was fed to a Schugi FX100 mixer at a rate of 365 g/min. The flow rate of zeolite was controlled by a loss in weight feeder. Perfume was fed to the mixer at a rate of 64 g/min. with the rate controlled by a positive displacement pump. The perfume was injected into the mixer through a two fluid nozzle. Liquid nitrogen was injected into the exhaust stream of the mixer to cool the product before it was collected.

4. Coating

The perfumed particles herein can optionally be coated with one or more protective layers, and agglomerated using, e.g., the coating material. Non-limiting examples of suitable coating materials include a coating matrix comprising polyols and/or diols as described in U.S. Pat. No. 5,691,303; a carbohydrate agglomerate or extrudate as disclosed in U.S. Pat. No. 5,648,328; a glassy coating comprising, e.g., starch hydrolysates, hydrogenated starch hydrolysates, sucrose, and glucose, as disclosed in U.S. Pat. No. 5,858,959; and a multiple coating including a glassy intermediate coating layer and a substantially non-tacky and/or non-sticky layer as described in U.S. Pat. No. 6,221,826. The perfumed particles herein can also optionally comprise a release barrier agent having cross-sectional area within the porous carrier being larger than the cross-sectional area of the pore openings of the porous carrier, as described in U.S. Pat. Nos. 6,048,830 and 6,245,732.

Mixtures of carbohydrates, gums, cellulose and cellulose derivatives and proteins are also suitable for use in coating the perfumed particles. Preferred coating materials are starches or modified starches such as CAPSUL™ commercially available from National Starch, cellulose and cellulose derivatives such as hydroxy propyl methyl cellulose, other carbohydrates such as sucrose and fructose, natural polymers such as gum arabic and guar gum, natural proteins, and water-soluble polymers such as polyethylene glycol.

The coating may include optional additive ingredients such as plasticizers, anti-agglomeration agents, and mixtures thereof. The optional plasticizers include sorbitol, polyethylene glycol, propylene glycol, low molecular weight carbohydrates and the like with a mixture of sorbitol and polyethylene glycol and low molecular weight polyols being the most preferred. The plasticizer is employed at levels of from about 0.01% to about 5%. The anti-agglomeration agents according to the present invention are preferably surfactants and are included at low levels of less than about 1% of the external coating. Suitable surfactants for use in the present invention include TWEEN™ 80 commercially available from Imperial Chemicals, Inc. (ICI). Any other modifiers contemplated by those of skill in the art would also be suitable for use in the coating materials of the present invention. Coating compositions are described in greater detail in PCT Publication No. WO 01/40430, Marin, et al., published Jun. 6, 2001 and in U.S. patent application No. 60/26895, Dihora, et al. filed Feb. 12, 2001, both of which are incorporated herein by reference.

When used, the coating may be applied to the perfumed particles by mixing the perfumed particles into a solution of modified starch and agitated to form an emulsion. The emulsion is then spray-dried using a spray dryer having a spraying system such as co-current with a spinning disk, with vaneless disk, with vaned disk or wheel or with two-fluid mist spray nozzle. Typical conditions involve an inlet temperature of from about 120° C. to about 220° C. and an outlet temperature of from about 50° C. to about 220° C. The resulting coated particles are discrete particles having particle size of from about 3 to about 100 microns as measured by standard particle size analysis technique.

III. Optional Components

Optional Soil Release Polymer

Optionally, the compositions herein contain from about 0.01% to about 10%, preferably from about 0.1% to about 5%, more preferably from about 0.1% to about 2%, of a soil release agent. Preferably, such a soil release agent is a polymer. Polymeric soil release agents useful in the present invention include copolymeric blocks of terephthalate and polyethylene oxide or polypropylene oxide, and the like. U.S. Pat. No. 4,956,447, Gosselink, et al., issued Sep. 11, 1990, discloses specific preferred soil release agents comprising cationic functionalities, said patent being incorporated herein by reference.

A preferred soil release agent is a copolymer having blocks of terephthalate and polyethylene oxide. More specifically, these polymers are comprised of repeating units of ethylene and/or propylene terephthalate and polyethylene oxide terephthalate at a molar ratio of ethylene terephthalate units to polyethylene oxide terephthalate units of from about 25:75 to about 35:65, said polyethylene oxide terephthalate containing polyethylene oxide blocks having molecular weights of from about 300 to about 2000. The molecular weight of this polymeric soil release agent is in the range of from about 5,000 to about 55,000.

U.S. Pat. No. 4,976,879, Maldonado, et al., issued Dec. 11, 1990, discloses specific preferred soil release agents that can also provide improved antistat benefit, said patent being incorporated herein by reference.

Another preferred polymeric soil release agent is a crystallizable polyester with repeating units of ethylene terephthalate containing from about 10% to about 15% by weight of ethylene terephthalate units together with from about 10% to about 50% by weight of polyoxyethylene terephthalate units, derived from a polyoxyethylene glycol of average molecular weight of from about 300 to about 6,000, and the molar ratio of ethylene terephthalate units to polyoxyethylene terephthalate units in the crystallizable polymeric compound is between about 2:1 and about 6:1. Examples of this polymer include the commercially available materials Zelcon® 4780 (from DuPont) and Milease® T (from ICI).

A more complete disclosure of these highly preferred soil release agents is contained in European Pat. Application 185,427, Gosselink, published Jun. 25, 1986, incorporated herein by reference.

Other Optional Ingredients

The present invention can include other optional components (minor components) conventionally used in textile treatment compositions, for example, anti-oxidants, colorants, preservatives, optical brighteners, opacifiers, stabilizers such as guar gum and polyethylene glycol, anti-shrinkage agents, anti-wrinkle agents, soil release agents, fabric crisping agents, reductive agents, spotting agents, germicides, fungicides, anti-corrosion agents, antifoam agents, and the like.

IV. Usage

The substrate embodiment of this invention can be used for imparting the above-described composition to fabric to provide softening, antistatic effects and improved perfume deposition on fabric in an automatic laundry dryer. Generally, the method of using the composition of the present invention comprises: commingling pieces of damp or dry fabric by tumbling the fabric under heat in an automatic clothes dryer with an effective amount of the composition. Preferably, the composition has a viscosity of less than about 2000 cps at 100° F. (38° C.) and a melting point greater than about 25° C. and more preferably from about 35° C. to about 100° C. such that the composition is flowable at dryer operating temperatures. This composition comprises from about 3% to about 90%, preferably from about 5% to about 90%, of the quaternary ammonium agent selected from the above-defined cationic fabric softeners and mixtures thereof, from about 0.1% to about 95%, preferably from about 3% to about 75%, more preferably from about 5% to about 60% of the above-defined co-softener.

The present invention further relates to improved dryer-activated fabric softener compositions that are either (A) incorporated into articles of manufacture in which the compositions are, e.g., on a substrate, or are (B) in the form of particles (including, where appropriate, agglomerates, pellets, and tablets of said particles). Such compositions contain from about 30% to about 95% of normally solid, dryer-softenable material, typically fabric softening agent, containing an effective amount of unsaturation.

In the specification and examples herein, all percentages, ratios and parts are by weight unless otherwise specified and all numerical limits are normal approximations.

The following examples illustrate the articles and compositions of this invention, but are not intended to be limiting thereof.

EXAMPLES

Dryer-activated fabric softening compositions according to the present invention include the following:

| Component | Ex. 1 | Ex. 2 |
|---|---|---|
| DEQA (1) | 38.42 | 39.26 |
| Amine/Fatty Acid Salt (2) | 19.21 | 19.63 |
| Clay (3) | 3.07 | 2.62 |
| Neat Perfume | 2.23 | 1.47 |
| Zeolite | 9.80 | 12.98 |
| Complexed Perfume | 1.73 | 2.29 |
| Substrate | 25.55 | 21.76 |

(1) Di-(soft-tallowyloxyethyl) hydroxyethyl methyl ammonium methyl sulfate
(2) Dimethyl stearyl amine/stearic acid salt
(3) Calcium Bentonite Clay, Bentonite L, sold by Southern Clay Products Preparation of Coating Mix The compositions of the present invention may be produced via the following process:

A batch of approximately 200 g is prepared as follows: Approximately 8 g of color care agent is combined with high shear mixing with about 98 g of pre-melted softeners in a vessel immersed in a hot water bath to maintain the temperature between about 70–80° C. to form a coating mixture. In a separate container, perfumed particles are prepared as described above. Optionally, a complex of cyclodextrin and perfume can be prepared and added to the perfumed particles. A complex blend comprising perfumed particles and softener compounds is prepared. The complex blend is milled in a ball mil to reduce particle size. Approximately 90 g of the complex blend is added to the coating mixture with blending. Clay (8 g) is mixed in to achieve the desired viscosity. Approximately 3 g of free perfume is added to the formula and the mixture is blended until homogeneous.

Preparation of Fabric Conditioning Sheets

The coating mixture is applied to pre-weighed substrate sheets (approx. 1 g) of about 6.75 inches×about 12 inches (approximately 17 cm×30 cm) dimensions. The substrate sheets are comprised of about 4-denier spun bonded polyester. A small amount of the formula is placed on a heated metal plate with a spatula and then is spread evenly with a wire metal rod. A substrate sheet is placed on the metal plate to absorb the coating mixture. The sheet is then removed from the heated metal plate and allowed to cool to room temperature so that the coating mix can solidify. The sheet is weighed to determine the amount of coating mixture on the sheet. The target sheet weight is approximately 3.5 g. If the weight is in excess of the target weight, the sheet is placed back on the heated metal plate to remelt the coating mixture and remove some of the excess. If the weight is under the target weight, the sheet is also placed on the heated metal plate and more coating mixture is added.

V. Packaging

Where perfume is absorbed and/or adsorbed onto porous inorganic carrier particles such as zeolite, the perfume will be desorbed upon adsorption of water, especially water vapor. Water vapor can effectively displace 95–98% of the perfume entrapped inside the zeolite cavity. The stability of the compositions and articles and their ability to effectively release the perfume components during use requires that such materials be protected from atmospheric moisture with a package having specific moisture barrier characteristics.

Selecting packaging material for the perfumed particles can be determined by the following steps. First, determine the critical amount of water that can be adsorbed or absorbed by the fabric conditioning article without premature loss of perfume. The loss of perfume can be quantified by an extraction method used to measure the total perfume composition of an article. Water absorption may be determined by exposing the composition/article to constant humidity and determining the mass gained over time. Note, that by coating or agglomerating the perfumed particles with a coating material as described above may lower the sensitivity of the carrier to moisture exposure. Evaluate the performance (analytical and/or sensory) of each fabric conditioning article to determine the critical quantity of water. Second, determine the surface area of the package in which the perfume articles will be packaged and sold in the trade as well as the in-trade stability requirement, such as the number of months that the finished product is likely to remain in the package prior to use. The maximum moisture vapor transmission rate (MVTR) for the composition/article may be calculated using the following equation:

$$MVTR = (\text{Critical Mass of Water})/(\text{Surface Area of Package})/(\text{in-trade stability required})$$

$$[=] g\ H_2O/m^2/\text{day}$$

Tabulated values of MVTR provided in technical references generally report data determined at about 28–38° C., and about 80%–90% relative humidity such that they represent worse case scenario ambient conditions. Selecting the packaging material under these conditions will ensure long-term stability of the packaged sheet.

Preferably, the sheet is packaged so that moisture penetration must occur through a continuous layer moisture barrier, and the moisture vapor transmission rate of the layer is less than about 1.0 g $H_2O/\text{day}/m^2$, preferably less than about 0.5 g $H_2O/\text{day}/m^2$, more preferably less than about 0.3 g $H_2O/\text{day}/m^2$, and even more preferably is about 0.1 g $H_2O/\text{day}/m^2$ to ensure article stability. Laminated films are also useful in achieving the desired moisture barrier level.

Films that are permeable to water vapor will not be sufficient to ensure stability. Determination of effective packaging materials must be done on a case-by-case basis since perfume materials will have various odor detection thresholds, and performance benefits that may be detected even after about 20–40% of the oil is lost from the zeolite. To ensure long-term stability of about 9 to about 12 months in a sealed package, preferred packaging materials will include laminated films, metallized films and foil materials, glass, and other materials that are capable of providing the described moisture transfer barrier. Such barrier materials may be used as liners and overwraps for other packaging such as cartons, tubs and the like. Alternatively, depending on the sensitivity of the fabric conditioning articles, packaging in polymeric materials, like thermoformed tubs is also envisioned. Preferred foil materials are metallized films in either single layer or laminated form.

It is envisioned that packaging made from such films will have an opening that is resealable. The following U.S. Patents describe various resealable packages that comprise a moisture impermeable film and various methods for manufacturing same: U.S. Pat. No. 4,552,269, issued to Chang on Nov. 12, 1985; U.S. Pat. No. 4,616,470, issued to Nakamura on Oct. 14, 1986; U.S. Pat. No. 4,651,874, issued to Nakamura on Mar. 24, 1987; U.S. Pat. No. 4,679,693, issued to Forman on Jul. 14, 1987; U.S. Pat. No. 4,723,301 issued to Chang on Feb. 2, 1988; U.S. Pat. No. 4,790,436 issued to Nakamura on Dec. 13, 1988; U.S. Pat. No. 4,840,270 issued on Jun. 20, 1989; U.S. Pat. No. 4,863,064 issued to Dailey, III on Sep. 5, 1989; U.S. Pat. No. 5,688,394 issued to McBride, Jr. et al., on Nov. 18, 1997; U.S. Pat. No. 5,725,311 issued to Ponsi et al., on Mar. 10, 1998; U.S. Pat. No. 5,824,380 issued to Hagen on Oct. 20, 1998; U.S. Pat. No. 5,938,013 issued to Palumbo et al. on Aug. 17, 1999; U.S. Des. Pat. No. D447,054 issued to Hill on Aug. 28, 2001; and U.S. Pat. No. 6,309,105 issued to Palumbo on Oct. 30, 2001, all of which are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dryer added fabric conditioning article comprising:
   a) a substrate in the form of a sheet; and
   b) a fabric conditioning composition disposed on said sheet, said fabric conditioning composition comprising:
      i) at least about 1% by weight of a fabric conditioning active;
      ii) perfumed particles, said perfumed particles having porous inorganic carrier particles and a perfume composition absorbed and/or adsorbed on said carrier particles;
   wherein said perfume composition comprises less than 30% by weight of the perfume composition, of unstable perfume ingredients; wherein the unstable perfume ingredients comprise at least one of the following: damascenone; decyl aldehyde; dihydro iso jasmonate; helional; ionone gamma methyl; linalool; bucinal; paramethyl acetophenone; phenyl ethyl alcohol; or undecavertol; and
   wherein said perfumed particles comprise a coating encapsulating at least a portion of said perfumed particles; wherein said coating comprises a polysaccharide, or derivative thereof.

2. The article of claim 1, wherein said fabric conditioning active is cationic fabric softener.

3. The article of claim 2, wherein said cationic fabric softener is a diester quaternary ammonium compound.

4. The article of claim 1, wherein the porous inorganic carrier particles comprise a zeolite, clay or mixture thereof.

5. The article of claim 4, wherein the zeolite comprises zeolite X, zeolite Y or mixtures thereof.

6. The article of claim 1, wherein said perfume composition comprises less than 15% by weight of the perfume composition, of unstable perfume ingredients.

7. The article of claim 6, wherein said perfume composition comprises less than 8% by weight of the perfume composition, of unstable perfume ingredients.

8. The article of claim 7, wherein said perfume composition comprises less than 6% by weight of the perfume composition, of unstable perfume ingredients.

9. The article of claim 8, wherein said perfume composition comprises less than 3% by weight of the perfume composition, of unstable perfume ingredients.

10. The article of claim 9, wherein said perfume composition comprises less than 1% by weight of the perfume composition, of unstable perfume ingredients.

11. The article of claim 1, wherein said coating comprises a starch or derivative thereof.

12. The article of claim 1, further comprising a cyclodextrin/perfume complex, neat perfume, pro-fragrance, soil release polymer, clay, and mixtures thereof.

13. The article of claim 1, wherein said composition has a thermal softening point of from about 35° C. to about 100° C.

14. The article of claim 1, wherein the substrate comprises a non-woven fabric comprising a polymeric material.

15. The article of claim 14, wherein the substrate comprises a polyester or derivative thereof.

16. The article of claim 1, further comprising a package for enclosing the article, the package having a moisture barrier.

17. The article of claim 16, wherein said moisture barrier has a water vapor transmission rate of less than about 1.0 g $H_2O/day/m^2$.

18. The article of claim 17, wherein said package comprises a film.

19. The article of claim 18, wherein said film comprises a metal.

20. The article of claim 16, further comprising a set of instructions associated with the package, said instructions comprising an instruction to contact wet fabrics with the article to obtain prolonged dry fabric odor from said perfume composition.

21. The article of claim 20, wherein said set of instructions comprise an instruction to place the fabric softening article with the wet fabrics in a laundry dryer and to operate the dryer.

22. A dryer added fabric conditioning article comprising:
   a) a substrate in the form of a sheet; and
   b) a fabric conditioning composition disposed on said sheet, said fabric conditioning composition comprising:
      i) at least about 1% by weight of a fabric conditioning active;
      ii) perfumed particles, said perfumed particles having porous inorganic carrier particles and a perfume composition absorbed and/or adsorbed on said carrier particles;
   wherein said perfume composition comprises less than 30% by weight of the perfume composition, of unstable perfume ingredients; wherein the unstable perfume ingredients comprise at least one of the following: damascenone; decyl aldehyde; dihydro iso jasmonate; helional; ionone gamma methyl; linalool; bucinal; paramethyl acetophenone; phenyl ethyl alcohol; or undecavertol; and
   wherein said perfumed particles comprise a coating encapsulating at least a portion of said perfumed particles; wherein said coating comprises a polysaccharide, or derivative thereof; and
   c) a package for enclosing the article, the package having a moisture barrier.

23. The article of claim 22, wherein said moisture barrier has a water vapor transmission rate of less than about 1.0 g $H_2O/day/m^2$.

24. The article of claim 23, wherein said package comprises a film.

25. The article of claim 24, wherein said film comprises a metal.

26. A method of depositing a perfume composition on fabric, said method comprising the step of contacting fabric with an article according to claim 1.

* * * * *

UNITED STATES PATENT AND TRADEMARK OFFICE
CERTIFICATE OF CORRECTION

PATENT NO.      : 7,071,157 B2
APPLICATION NO. : 10/903674
DATED           : July 4, 2006
INVENTOR(S)     : Bienvenido Alvarez Santos et al.

It is certified that error appears in the above-identified patent and that said Letters Patent is hereby corrected as shown below:

<u>Column 6</u>

Last line of formula under heading Unsaturated should read:

-- $(HOCH_2CH_2)(CH_3)N^+(CH_2CH_2OC(O)R^2)_2(CH_3SO_4)^-$ --.

<u>Column 8</u>

Line 26, delete "dilaurylmethyl amine" and insert -- dilaurylmethylamine --.

Lines 26-27, delete "distearylmethyl amine" and insert -- distearylmethylamine --.

<u>Column 13</u>

Line 52, delete "decal actone" and insert -- decalactone --.

<u>Column 14</u>

Line 10, delete "sandal wood" and insert -- sandalwood --.

<u>Column 17</u>

Line 52, delete "linally pyruvate" and insert -- linallyl pyruvate --.

<u>Column 18</u>

Line 63 insert -- (a hyphen) -- after the word trimethyl.

Line 64, delete "methyl anthranilate" and insert -- methylanthranilate --.

UNITED STATES PATENT AND TRADEMARK OFFICE
CERTIFICATE OF CORRECTION

PATENT NO. : 7,071,157 B2
APPLICATION NO. : 10/903674
DATED : July 4, 2006
INVENTOR(S) : Bienvenido Alvarez Santos et al.

It is certified that error appears in the above-identified patent and that said Letters Patent is hereby corrected as shown below:

<u>Column 21</u>

Line 9, delete "0.2%" and insert -- 2% --.

Signed and Sealed this

First Day of January, 2008

JON W. DUDAS
*Director of the United States Patent and Trademark Office*